(12) United States Patent
Mackintosh et al.

(10) Patent No.: US 7,713,694 B2
(45) Date of Patent: May 11, 2010

(54) METHOD OF ENHANCING FLUORESCENCE

(75) Inventors: James Alexander Mackintosh, Thornleigh (AU); Duncan Adam Veal, Turramurra (AU); Peter Helmuth Karuso, Epping (AU); Daniel Richard Coghlan, Abbotsford (AU); Hung-Yoon Choi, Rydalmere (AU)

(73) Assignee: Fluorotechnics Pty Limited, North Ryde (AU)

( * ) Notice: Subject to any disclaimer, the term of this patent is extended or adjusted under 35 U.S.C. 154(b) by 752 days.

(21) Appl. No.: 11/235,931

(22) Filed: Sep. 26, 2005

(65) Prior Publication Data

US 2006/0094042 A1 May 4, 2006

Related U.S. Application Data

(63) Continuation-in-part of application No. PCT/AU2004/000370, filed on Mar. 25, 2004.

(30) Foreign Application Priority Data

Mar. 25, 2003 (AU) .............................. 2003901361

(51) Int. Cl.
*C12Q 1/68* (2006.01)
*C07H 21/00* (2006.01)
*C07H 21/02* (2006.01)
(52) U.S. Cl. .................. 435/6; 435/5; 435/7.1; 435/7.2; 536/23.1; 536/26.6
(58) Field of Classification Search .............. 435/5, 435/6, 7.1, 7.2; 536/23.1, 26.6
See application file for complete search history.

(56) References Cited

FOREIGN PATENT DOCUMENTS

| EP | 1 223 226 A2 | 7/2002 |
|---|---|---|
| WO | WO 01/81351 A1 | 11/2001 |
| WO | WO 02/40595 A1 | 5/2002 |

OTHER PUBLICATIONS

International Preliminary Examination Report for corresponding PCT.AU2004/000370 dated Jul. 5, 2005.
International Search Report for corresponding PCT/AU2004/000370 dated Jul. 19, 2004.
Bartoszek, et al.: "Versatile method employing basic techniques of genetic engineering to study the ability of low-molecular weight compounds to bind covalently with DNA in cell-free systems," *Analytical Biochemistry* 313: 53-59 (2003).
Bathale, et al.: "Energetic and binding properties of DNA upon interaction with dodecyl trimethylammonium bromide," *Nucleic Acids Research* 27 (4); 1001-1005 (1999).
Bell, et al.: "Epicocconone, A Novel Fluorescent Compound from the Fungus *Epicoccum nigrum*," *J. Am. Chem. Soc.* 125: 9304-0305 (2003).

(Continued)

*Primary Examiner*—Jezia Riley
(74) *Attorney, Agent, or Firm*—Marshall, Gerstein & Borun LLP

(57) ABSTRACT

A method of enhancing the fluorescence of and/or producing an increased Stokes' shift in a fluorescent dye comprising combining the dye with a base and/or a detergent is described. The method is suitable in chemical or biochemical techniques using fluorescent dyes, particularly techniques requiring staining or labeling of organic molecules, such as electrophoresis.

33 Claims, 27 Drawing Sheets

OTHER PUBLICATIONS

Bhairi, S.: *Detergents: A guide to the properties and uses of detergents in biological systems*, Calbiochem-Novabiochem Corporation, 2001.

Breadmore, et al.: "Microchip-Based Purification of DNA from Biological Samples," *Anal. Chem. 75*: 1880-1886 (2003).

Ferrari, et al.: "Application of the novel fluorescent dye Beljian red to the differentiation of *Giardia* cysts," *Journal of Microbiological Methods 52*: 133-135 (2003).

Harrington, et al.: "Binding to the yeast Swi4,6-dependent cell cycle box, CACGAAA, is cell cycle regulated in vivo," *Nucleic Acids Research 24*(4): 558-565 (1996).

Jaroszeski, et al.: "Detection and Quantitation of Cell-Cell Electrofusion Products by Flow Cytometry," *Analytical Biochemistry 216*: 271-275 (1994).

Kamp, et al.: "Rapid Flip-flop of Oleic Acid across the Plasma Membrane of Adipocytes," *The Journal of Biological Chemistry 278*(10): 7988-7995 (Mar. 7, 2003).

Kersten, et L.: "Generation of *Arabidopsis* protein chips for antibody and serum screening," *Plant Molecular Biology 52*: 999-1010 (2003).

Paulmurugan, et al.: "Molecular Imaging of Drug-Modulated Protein-Protein Interactions in Living Subjects," *Cancer Research 64*: 2113-2119 (Mar. 15, 2004).

Shapiro, H.: *Practical Flow Cytometry*, 4th ed. Wilet-Liss, Hoboken, NJ, 2003.

Graczyk et al., *Am. J. Trop. Med. Hyg. 68*(2), pp. 228-232 (2003).

A

B

A. 16 mM octylamine

B. 16 mM tris base

C. 16 mM butylamine

D. 16 mM aniline

E. 16 mM 1,3 diaminopropane

F. 16 mM ammonia

G. water

A  Time 0     B  46 h     C  167 h

A)  B)

A)  B)

Gel strip 1, 0.001 mM; Gel strip 2, 0.01 mM; Gel strip 3, 0.1 mM; Gel strip 4, 1 mM

METHOD OF ENHANCING FLUORESCENCE

CROSS REFERENCE TO RELATED APPLICATIONS

This is a continuation-in-part of International Application No. PCT/AU2004/000370 filed Mar. 25, 2004, which in turn claims the priority benefit of Australian Application Serial No. 2003901361 filed Mar. 25, 2003 the disclosures of which are hereby incorporated by reference.

TECHNICAL FIELD

This invention relates to a method of enhancing fluorescence, especially in organic molecules, such as proteins and nucleic acids, stained or labelled with fluorescent dyes.

BACKGROUND ART

Any discussion of the prior art throughout the specification should in no way be considered as an admission that such prior art is widely known or forms part of common general knowledge in the field.

Compounds that fluoresce have many uses and are known to be particularly suitable for biological applications where fluorescence is intrinsically more sensitive than absorption as the incidence and observed wavelengths are different. Fluorescence can be used for the detection of whole cells, cellular components, and cellular functions. For example, many diagnostic and analytical techniques require the samples to be fluorescently tagged so that they can be detected. This is achieved by using fluorescent dyes or probes which interact with a wide variety of materials such as cells, tissues, proteins, antibodies, enzymes, drugs, hormones, lipids, nucleotides, nucleic acids, carbohydrates, or natural or synthetic polymers to make fluorescent conjugates.

With synthetic fluorescent probes, ligands are frequently used to confer a specificity for a biochemical reaction that is to be observed and the fluorescent dye provides the means of detect or quantify the interaction. These applications include, among others, the detection of proteins (for example in gels, on surfaces or aqueous solution), cell tracking, the assessment of enzymatic activity and the staining of nucleic acids or other biopolymers.

Long wavelength absorbance usually increases the utility of a fluorescent probe since it reduces the interference from cellular autofluorescence and is less likely to cause photodamage of labelled biomolecules. Although lasers are particularly useful as a concentrated light source for the excitation of fluorescence, at present the output of powerful lasers is restricted to particular wavelengths of light. Compounds whose excitation spectrum coincide with laser output are therefore of high utility. The argon laser is the most common light source for excitation of fluorescence, and has principal output at 488 nm and a weaker output at 514 nm. Fluorescent compounds that are excited by either of these wavelengths are therefore of particular utility. YAG lasers (532 nm or 473) and HeNe (543 nm, 633 nm) are also becoming common.

Red fluorescent compounds are used extensively in many fields of biological study. Many of these, including Texas red, Tetramethyl rhodamine or red emitting BODIPY dyes require excitation at green wavelengths such as 542 nm. This limits their use in many applications, especially those where the argon-ion laser is used for excitation.

Compounds such as ethidium bromide, can be excited with light from the argon-ion laser, but are not generally suitable for tagging of organic molecules other than nucleic acids.

Other compounds such as phycoerythrin, can be excited using the argon-ion laser (488 nm), and emits in the orange wavelengths (ca 580 nm). Phycoerythrin, however, has poor stability and a high molecular weight (ca 240,000 Da) making it unsuitable for many applications such as cell tracking, labelling of nucleic acids or staining proteins.

For staining of proteins, there are a number of methods available. These methods can utilise non-fluorescent compounds, or fluorescent compounds. The most commonly used method utilises Coomassie blue (Bradford assay), which is non-fluorescent. Fluorescence-based protein-detection methods utilise fluorescent dyes, which form a complex with the protein and are intrinsically more sensitive than non-fluorescent methods. Fluorescent staining of proteins has a number of advantages over traditional Silver or Coomassie staining. These advantages include greater sensitivity, lower background interference and greater dynamic range.

For staining of nucleic acids such as DNA and RNA ethidium bromide as a fluorescent stain has been most widely used due to its cost effectiveness and high sensitivity (2 ng/ban of dsDNA). Its uses among researchers have been somewhat limited because it is thought to be carcinogenic. Other fluorescent nucleic acid stains are currently available for quantification of nucleic acids as well as gel staining however in use such stains also have significant disadvantages.

WO01/81351, incorporated herein by reference, describes fluorescent dye compounds based on a furo[3,2-g][2]benzopyran-2,9(9aH)dione core.

Fluorescent dyes are particularly useful in the field of electrophoresis. Electrophoresis allows the separation of charged biomolecules, such as DNA, RNA and/or proteins, by making use of the relative mobilities of the charged molecules in a gel matrix after the application of an electrical field. The distance moved by each molecule in the electrical field depends on the charge, shape and weight of the molecule.

The most commonly used gel matrix for the separation of proteins is polyacrylamide (PAGE electrophoresis). SDS-PAGE is a technique whereby proteins are treated with the anionic detergent sodium dodecyl sulfate (SDS) before electrophoresis. SDS denatures the proteins and coats them with a uniform negative charge. This means that separation is based solely on molecular weight, and SDS-PAGE is typically used to determine the molecular weights of proteins[1].

In contrast, nucleic acid bear a single negative charge for every nucleotide (MW approx 500 Daltons) so there is a reasonably constant mass/charge ratio. In the case of nucleic acids it is not necessary to normalise the charge with a detergent.

Whilst a number of fluorescent dyes are known in the art, there is still a need to improve the signal intensity, the signal to background ratio and the sensitivity of fluorescent dyes. There is an additional need to improve the stability of fluorescent complexes formed on an electrophoresis gel matrix.

It is an object of the present invention to overcome or ameliorate at least one of the disadvantages of the prior art, or to provide a useful alternative.

SUMMARY OF THE INVENTION

The present invention provides methods for enhancing the fluorescence of fluorescent dyes, producing an increased Stokes' shift (ie. a further increase in the usual difference between the excitation and emission wavelengths) and improving stability of fluorescent dye/organic molecule complexes thus increasing intensity and/or longevity of fluorescence of stored samples in solution or on gel matrices.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

As used herein, the term "enhancing the fluorescence" generally means increasing fluorescent emission from a fluorescent dye. The increase may be at the dye's usual emission wavelength or at a different wavelength. This may be evident by an increase in the fluorescent intensity, an increase in the signal to background ratio or an increase in the detection sensitivity limit of the fluorescent dye (i.e. greater sensitivity).

As used herein, the term "Stokes' shift" refers to the well-known phenomenon of a shift in the emission wavelength from the excitation wavelength of a fluorescent dye. The shift is towards a higher wavelength (i.e. a red shift).

As used herein, the term "azaphilone fluorescent dye" means any fluorescent dye which is obtained or is obtainable from a polyketide biosynthetic pathway. Examples of dyes obtainable from a polyketide biosynthetic pathway are described in WO01/81351, incorporated herein by reference.

Moreover, unless the context clearly requires otherwise, the term "fluorescent dye" refers to fluorescent dye compounds, as well as fluorescent complexes or conjugates formed when a fluorescent dye compound is associated with or conjugated with an organic molecule, such as a protein or a nucleic acid. Fluorescent complexes or conjugates may be formed with organic molecules by non-covalent and/or covalent interactions.

The present inventors have found that the presence of a base, particularly a nitrogen containing base, causes a shift in the usual emission wavelength of certain fluorescent dyes, particularly azaphilone fluorescent dyes, from green to red fluorescence. This Stokes' shift is advantageous because it shifts the emission wavelength of the fluorescent dye further from the excitation wavelength of a typical argon ion laser (488 nm). Long Stokes' shift fluorescent dyes are important biochemical reagents since their fluorescence emission may be detected with minimum interference from the excitation light source and are less prone to self-quenching as there is less overlap between excitation and emission profiles. Furthermore, long Stokes' shift dyes are less prone to interference from autofluorescence which is due to the presence of short Stokes' shift fluorophores present in many biological samples. Known fluorescent dyes having a long Stokes' shift are typically high molecular weight molecules, which severely limits their application as fluorescent labels due to poor permeability and proteolysis.

More significantly, in the present invention, the Stokes' shift, and/or the increase in Stokes' shift, can also be accompanied by an increase in signal intensity, which in turn leads to a higher signal to background ratio (i.e. a reduction in non-specific background fluorescence) and/or an increase in the detection sensitivity limit of the fluorescent dye. Therefore, the presence of the base significantly improves on known fluorescent techniques, and especially fluorescent staining techniques for the detection of organic molecules.

Further in the present invention, it has been found that the choice of base can influence the magnitude of increase in the Stokes' shift.

Preferably, the fluorescent dye is of the formula (Ia), or isomer thereof:

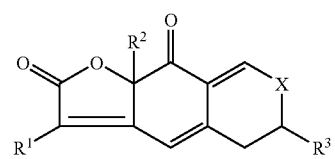

Preferably, X is O, $NR^4$ or C. Preferably, $R^1$ is a straight or branched chain $C_{1-20}$ conjugated alkenyl group optionally substituted 1-6 groups independently selected from hydroxy or oxo groups. Preferably, $R^2$ is a straight or branched chain $C_{1-20}$alkyl group. Preferably, $R^3$ is a straight or branched chain $C_{1-20}$alkyl group, optionally substituted with a hydroxyl group. Preferably, $R^4$ is N, O, straight or branched chain $C_{1-20}$alkyl and/or aryl group, optionally substituted with a hydroxyl, halide, amine, carboxyl, carboxyl related or heteroaryl group or groups.

Preferably, the dye is of formula (Ib), including isomers thereof:

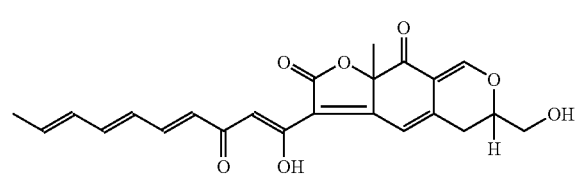

The compound of formula (Ib) is 5,6-dihydro-3-[(1Z,4E,6E,8E)-1-hydroxy-3-oxo-1,4,6,8-decatetraenyl]-6-hydroxymethyl-9a-methyl-2H-furo [3,2g][2]benzopyran-2-9 (9aH)-dione. However, this compound will be hereinafter referred to by its trivial name, which is "epicocconone".

In the context of the present invention isomers of compounds of formulae Ia and Ib include tautomers and stereoisomers among other isomers.

Epicocconone and epicocconone-containing dye mixtures and extracts are preferred.

The base used in the present invention is preferably selected from ammonia, and a variety of amines. Thus, the preferred base is a nitrogen-containing base. As used herein, the term "amine" refers to any compound containing one or more amino groups. Hence, the term includes monoamines, diamines, triamines etc. The amine may be primary, secondary, tertiary or quaternary. Further, salts of amines (e.g. HCl salts) are included within the meaning of the term "amine". Metal carbonates and metal hydrogen carbonates, or combinations thereof may also be used.

Preferably, the base is ammonia, a primary amine, a secondary amine, a tertiary amine, a quaternary amine salt, or a combination thereof. The base used in the present invention is preferably ammonia or $C_{1-20}$ amines and diamines, such as methylamine, ethylamine, propylamine, butylamine, ethylamine, propylamine, butylamine, pentylamine, hexylamine, heptylamine, octylamine, nonylamine, decylamine, undecylamine, dodecylamine and their isomers and allyl amine, aniline, benzylamine, 2-phenylethylamine, 4-phenylbutylamine, hydrazine and 1,2-diaminoethane, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,12-diaminododecane and their isomers and dimethylamine, diethylamine, dipropylamine, dibutylamine, dipentylamine, dihexylamine, dioctylamine, didecylamine, N-methylaniline, N-ethylaniline, N-propylaniline, N-butylaniline and their isomers and trimethylamine, triethylamine, tripropylamine, tributylamine, tripentylamine, trihexylamine, trioctylamine, tridecylamine, tridodecylamine and their isomers and tetramethylammonium acetate, tetramethylammonium bromide, tetramethylammonium carbonate, tetramethylammonium chloride, tetramethylammonium fluoride, tetramethylammonium formate, tetramethylammonium hydrogensulphate, tetramethylammonium iodide, tetramethylammonium iodide, tetramethylammonium nitrate, tetramethylammonium sulfate, tetraethylammonium acetate, tetraethylammonium bromide, tetraethylammonium chloride, tetraethylammonium cyanide, tetraethylammonium fluoride, tetraethylammonium hydroxide, tetraethylammonium iodide, tetraethylammonium nitrate, tetrapropylammonium bromide, tetrapropylammonium hydroxide, tetrabutylammonium hydroxide, tetrabutylammonium iodide, pyrrolidine, piperidine, pyridine, imidazole, indole, purine, quinoline, pyrimidine, pyrazole, tris(hydroxymethyl)aminomethane ("Tris") or aminododecylamine.

Preferably, the metal carbonates and metal hydrogen carbonates are salts of alkali and alkaline earth metals, such as sodium carbonate, potassium carbonate, sodium hydrogen carbonate etc. More preferably, the metal carbonate is sodium carbonate.

According to one aspect of the invention the fluorescent dye (Ia) may be combined with a base to afford a compound of the formula (IIa), including isomers thereof:

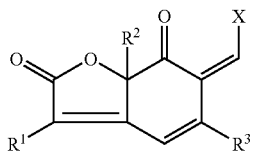

(IIa)

wherein $R^1$, $R^2$, $R^3$ are the same as set out for (1a). X is C, $NR^4R^5$, $OR^4$, $R^3$, $R^5$ are either H, N, O, straight or branch chain $C_{1-20}$ alkyl, alkenyl, alkynyl and/or aryl group, optionally substituted with a hydroxyl, halide, amine, carboxyl, carboxyl related or heteroaryl group or groups. According to another aspect of the invention, the fluorescent dye (Ib) combines with a base to afford another fluorescent dye, which is of the formula (IIb), including isomers thereof:

(IIb)

wherein X is C, $NR^4R^5$ or $OR^4$. According to a further aspect of the invention, when the fluorescent dye (Ib) combines with n-butylamine the resulting dye has the formula (IIc), including isomers thereof:

(IIc)

Preferably, the method of the present invention is part of any chemical or biochemical technique using a fluorescent dye. Typical examples of chemical or biochemical technique where the present invention may be used are electrophoresis, flow cytometry, pH sensing, analysing protein-protein interactions, fluorescent protein quantitation, assaying protein arrays or protein chips, assaying gene arrays or gene chips, assaying/detecting/quantifying nucleic acids, fluorescence microscopy and fluorescent antibody staining, and the like[2-10, 14-16]. The relevant publications are incorporated herein by reference.

In one embodiment, the method described above is part of a method of staining and/or labelling an organic molecule, the method comprising forming a fluorescent complex between the organic molecule and the fluorescent dye, wherein the fluorescent complex is formed in the presence of a base and/or the fluorescent complex is treated with a base after its formation.

In another embodiment, the method described above comprises forming a fluorescent complex between the organic molecule and the fluorescent dye in the presence of a base and/or a detergent, and/or the fluorescent complex is treated with a base and/or detergent after its formation.

The organic molecule may be any molecule requiring staining or labelling by a fluorescent dye. However, the organic molecule is typically a protein, a peptide, a nucleotide or a nucleic acid (DNA or RNA and the like), which may or may not be included in another complex molecule such as an enzyme, a cellular receptor, a growth factor, an antibody, or be part of a tissue, an organ or a cell.

The base may be added to a solution containing the organic molecule before forming the fluorescent complex. The final concentration of base in this solution is preferably between 0.001 and 10%, more preferably between 0.02% and 5%. The % values are given either as w/v or v/v amounts, depending on the base used. Alternatively, the final concentration of base is preferably between 100 μM and 2 M, more preferably between 1 mM and 100 mM.

In another embodiment, the base is added to the fluorescent complex after it has been formed. The concentrations of base used in this embodiment will be similar to those described above.

In one aspect, the method of the present invention is used as part of a method of mobilising and detecting an organic molecule on a matrix, such as electrophoresis separation on a gel matrix. As described above, electrophoresis is typically carried out on a polyacrylamide gel matrix and is used for separation and/or molecular weight determination of proteins. A protein solution is generally loaded onto the gel and an electrical field applied, which causes the negatively charged molecules to migrate towards the anode. In SDS-PAGE electrophoresis, the protein is complexed with an anionic detergent, such as SDS, to give a uniform negative charge over the protein. Both conventional PAGE electrophoresis and SDS-PAGE electrophoresis methods are included within the scope of the present invention.

It is also contemplated within the present invention that the organic molecule and/or gel matrix may be treated with the base after electrophoresis. For example, the post-electrophoresis gel may be washed with the base either before or after being treated with the fluorescent dye. Post-electrophoresis washing is preferably performed using fatty amines (C4-C20 primary amines) or ammonia, since these bases will tend to partition to SDS micelles surrounding separated proteins in the gel. Typically, the gel is given 2×10 minute washes with a basic solution of appropriate concentration, although the number of washes and wash time will vary depending on the base used, the size of the gel plate, the concentration of base etc.

In another embodiment, the detergent, whether used separately or in combination with the base, may be added to a solution containing the organic molecule before forming the fluorescent complex. Typically this approach may be used where the organic molecule is a protein or a peptide. The final concentration of detergent in this solution is preferably between 0.001% and 10%, more preferably between 0.01 and 1%. The % values are given either as w/v or v/v amounts, depending on the detergent used. Alternatively, the final concentration of detergent is preferably between 20 μM and 200 mM, more preferably between 200 μM and 20 mM.

In yet another embodiment, the detergent is added to the fluorescent complex (the complex may have been formed in the presence of a base or be exposed to a base after its formation) after it has been formed. This approach would typically be used where the organic molecule is a nucleic acid, but it may also be used with proteins. The concentrations of detergent used in this embodiment will be similar to those described above.

Similar to the methods described above for proteins, the methods of the present invention can be used as part of methods of mobilising and detecting nucleic acids (eg. DNA or RNA and the like) either in solution or following electrophoretic separation on a gel matrix. Electrophoresis of nucleic acids is typically carried out on an agarose or polyacrylamide gel matrix and is used for separation, purification and/or molecular weight determination of nucleic acids. A nucleic acid solution is generally loaded onto the gel and an electrical field applied, which causes the migration of the nucleic acids towards the anode, similar to the protein electrophoretic technique described above.

As for the base described above, the detergent used in the present invention may be incorporated at any suitable stage of electrophoresis prior to detection of the fluorescent complex. For example, in case of methods used with proteins, the detergent may be admixed with the protein (preferably the detergent is SDS but other examples are provided herein) in solution before being loaded onto the gel. Alternatively, the gel matrix may be washed with the detergent, in the absence or presence of a base, after electrophoresis. This latter technique is typically used with nucleic acid separation and analysis.

In a further aspect of the present invention, the methods described above further comprises treating the fluorescent complex with an acid. This further treatment step is particularly suitable for fluorescent complexes formed on electrophoresis gels but may also be used for in-solution complexes.

Treatment with an acid, surprisingly, stabilises the fluorescent complex, further increases the fluorescent intensity, prevents or minimises the loss of fluorescence and/or further increases the signal to background ratio of the fluorescent complex. The acid may be selected from a mineral acid, an organic acid, or combinations thereof. Suitable mineral acids are sulfuric acid, hydrochloric acid, nitric acid, phosphoric acid, orthophosphoric acid. Suitable organic acids are alkanoic acids (e.g. a $C_{1-20}$ alkanoic acid), halogenoalkanoic acids (e.g. a $C_{1-20}$ alkanoic having 1, 2, 3, 4, 5 or 6 groups selected from F, Cl, Br or I), ascorbic acid or triflic acid. Preferably, the acid is sulfuric acid, acetic acid, propionic acid, ascorbic acid, hydrochloric acid, orthophosphoric acid, trifluoroacetic acid, trichloroacetic acid or chloroacetic acid.

The concentration of the acid used is typically between about 0.01% and 20% (v/v), preferably between about 0.02% and 10% (v/v). Alternatively, the concentration of acid is typically between about 0.1 mM and 2 M depending on the acid used, although acid concentrations of about 10 mM are generally preferred.

In a typical acid treatment step, an electrophoresis gel is incubated for about 10 minutes in acid (e.g. 10 mM sulfuric acid) prior to imaging.

Preferably, the fluorescent complex formed in the present invention is detected using any standard technique known in the art. Typically, the fluorescence of the fluorescent complex is detected by transillumination, spectroscopy, microscopy, scanning, photography or cytometry.

The present invention also provides a method of mobilising and detecting proteins comprising the steps of:
  (a) applying a solution of a protein to a matrix;
  (b) mobilising the protein on the matrix;
  (c) forming a fluorescent complex between the mobilised protein and a fluorescent dye as described above; and
  (d) detecting the so-formed fluorescent complex;

wherein the fluorescent complex is formed in the presence of a base and/or a detergent.

The preferred detergent to be used with proteins is an anionic detergent.

Another embodiment of the invention contemplates the above method in which the treatment of the fluorescent complex with a base and/or detergent is conducted after its formation.

Preferably, the matrix used for proteins and peptides is a polyacrylamide gel matrix and the method is PAGE electrophoresis or SDS-PAGE electrophoresis.

The present invention further provides a method of mobilising and detecting nucleic acids comprising the steps of:
  (a) applying a solution of a nucleic acid to a matrix;
  (b) mobilising the nucleic acid on the matrix;
  (c) forming a fluorescent complex between the mobilised nucleic acid and a fluorescent dye as described above; and
  (d) detecting the so-formed fluorescent complex;

wherein the fluorescent complex is formed in the presence of a base and/or a detergent.

The preferred detergent for use with nucleic acids is a cationic detergent.

Another embodiment of the invention contemplates the above method in which the treatment of the fluorescent complex with a base and/or detergent is conducted after its formation.

Preferably, the matrix used with nucleic acids is an agarose gel matrix.

The above methods also contemplate a step in which the matrix is treated with an acid as the final step. The acid-treated matrices may be stored for periods of time without significant loss of fluorescence intensity.

The present invention also provides a fluorescent compound or complex obtainable by combining a fluorescent dye as described above with a base and/or detergent as described above.

The present invention also provides a composition comprising of a fluorescent dye as described above, a base and/or a detergent as described above. The composition may further include an organic molecule, such as a protein and/or a nucleic acid.

The present invention also provides a kit comprising of a fluorescent dye as described above, a base and/or a detergent as described above. The kit may further include an organic molecule, such as a protein and/or a nucleic acid.

Figure 24:
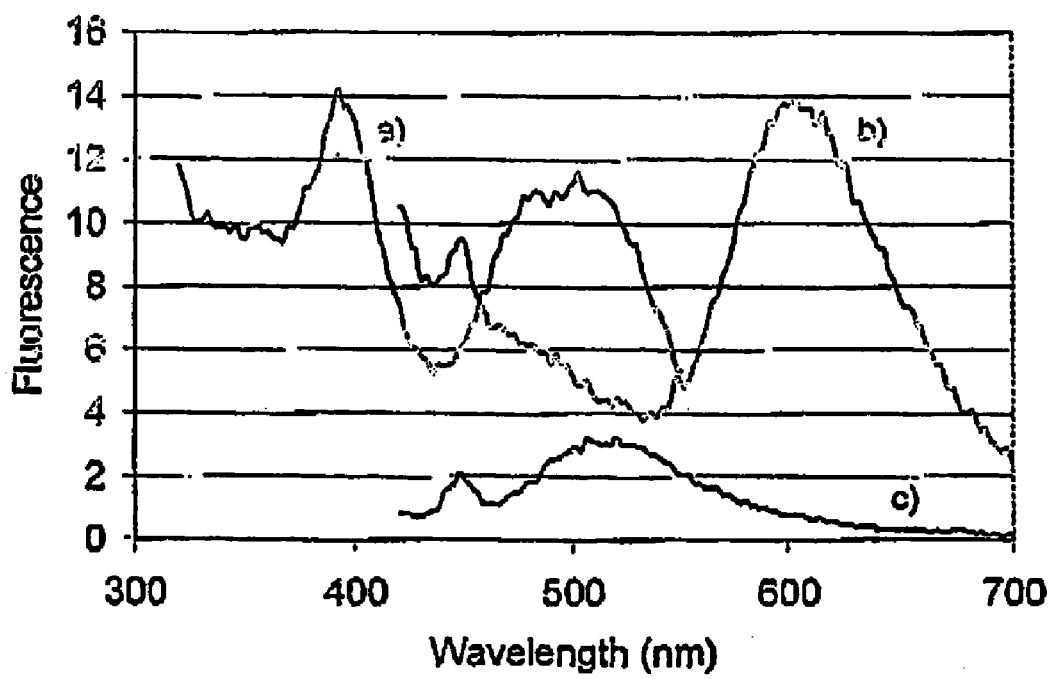

FIG. 24: a) Epicocconone with SDS and TRIS: excitation 320-550 nm/emission 600 nm and b) excitation 390 nm/emission 420-700 nm compared with c) Epicocconone at the same concentration without SDS and without TRIS: excitation 390 nm/emission 420-700 nm.

Figure 25:
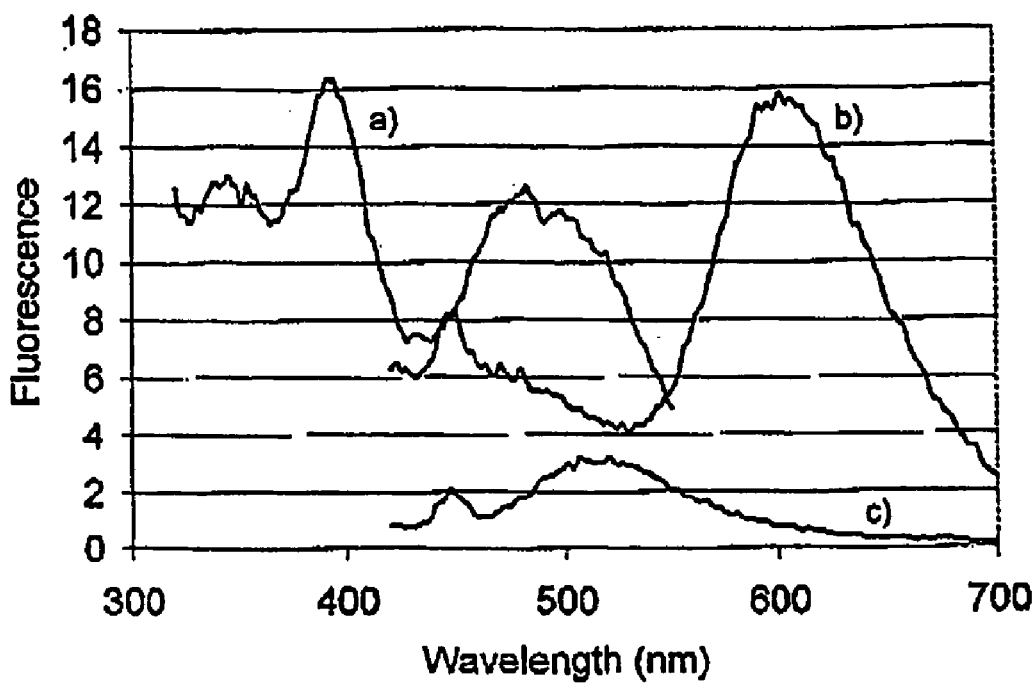

FIG. 25: a) Epicocconone with SDS and benzylamine: excitation 320-550 nm/emission 600 nm and b) excitation 390 nm/emission 420-700 nm compared with c) Epicocconone at the same concentration without SDS and without benzylamine: excitation 390 nm/emission 420-700 nm.

Figure 26:
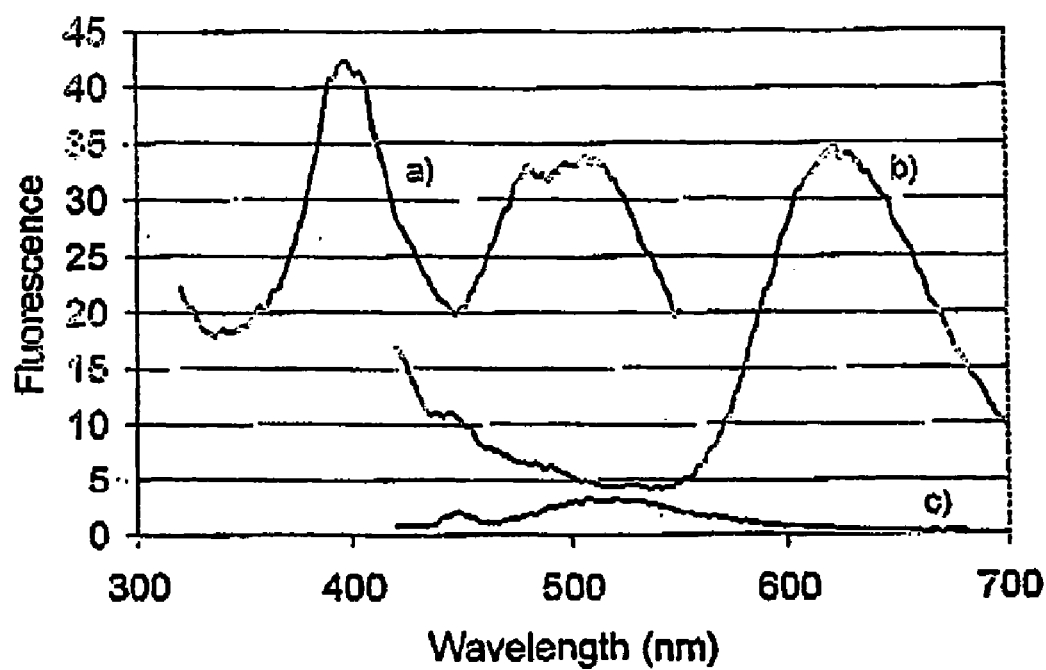
Figure 27:
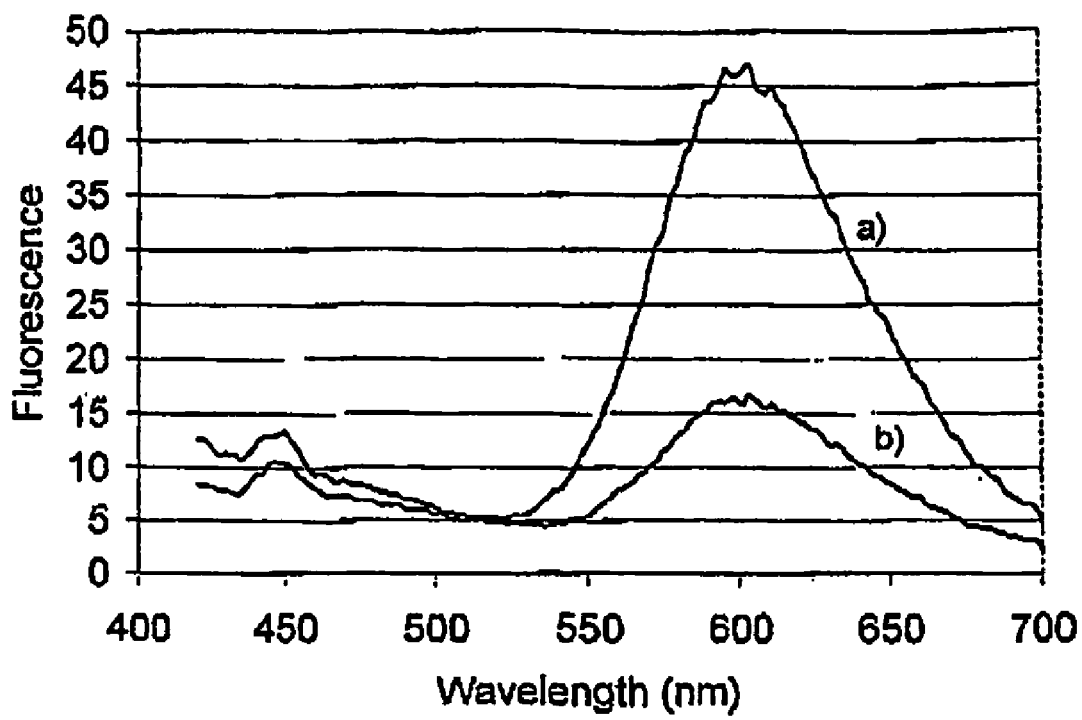

FIG. 26: a) Epicocconone with SDS and aniline: excitation 320-550 nm/emission 620 nm and b) excitation 390 nm/emission 420-700 nm compared with c) Epicocconone at the same concentration without SDS and without aniline: excitation 390 nm/emission 420-700 nm FIG. 27: Excitation 390 nm/emission 420-700 nm of a) Epicocconone with SDS, DNA and 1,3-diaminopropane after 1 day and b) Epicocconone with SDS, DNA and 1,3-diaminopropane.

Figure 28:
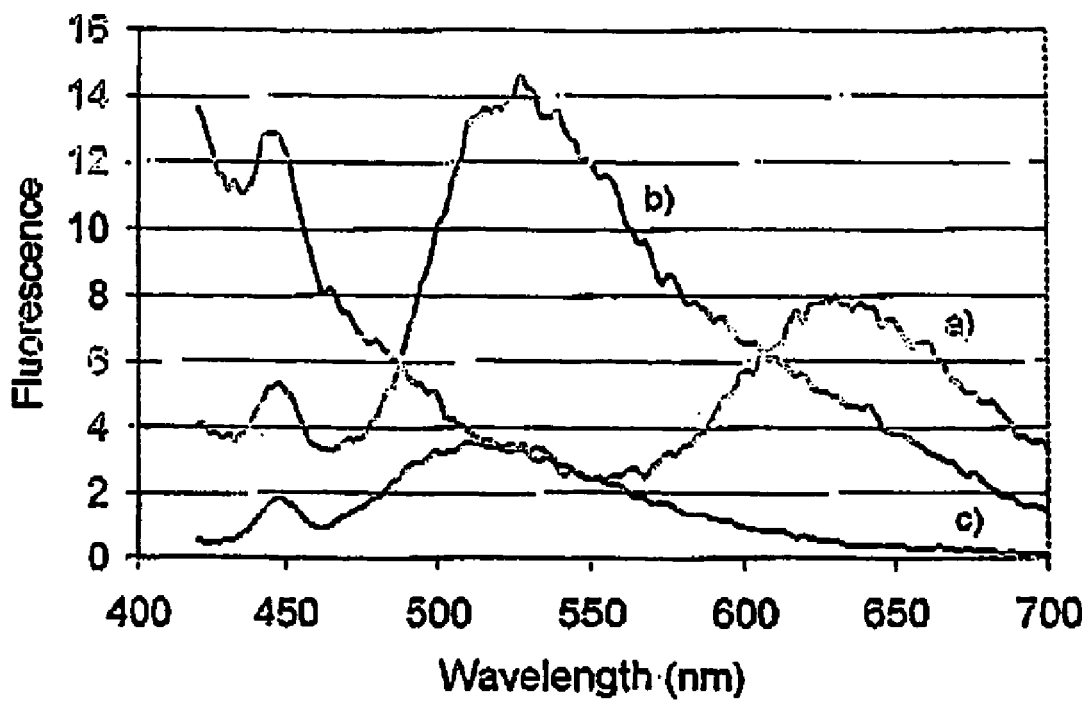

FIG. 28: Excitation 390 nm/emission 420-700 nm of a) Epicocconone with CHAPS and ammonia, b) Epicocconone with CHAPS and without ammonia and c) Epicocconone without CHAPS and without ammonia.

Figure 29:
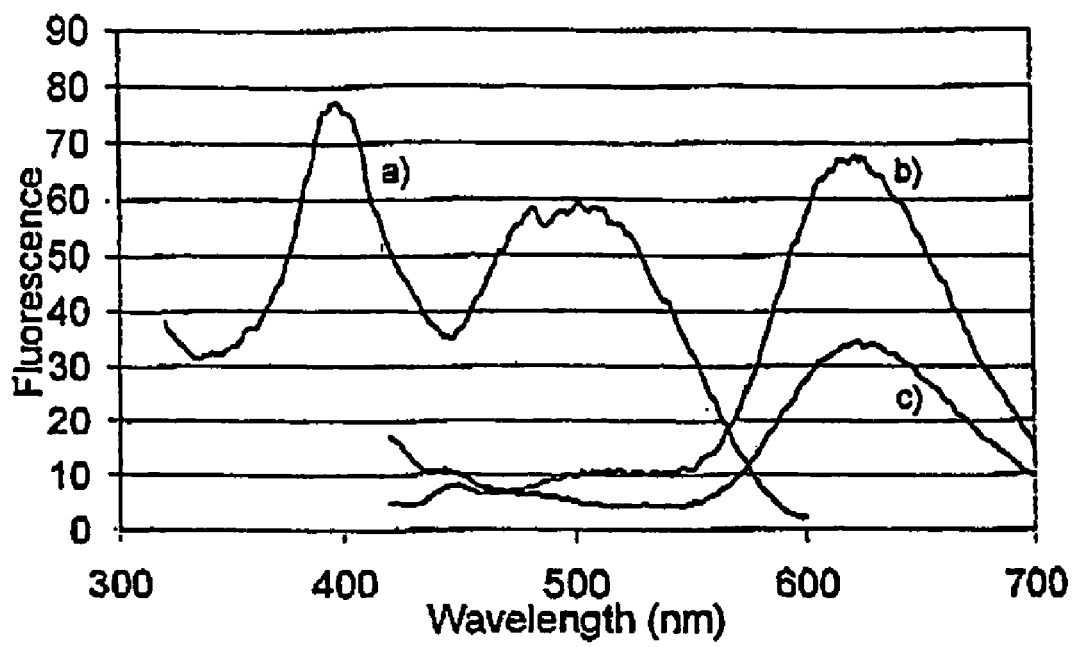

FIG. 29: a) Epicocconone with SDS, acetic acid and aniline: excitation 320-600 nm/emission 621 nm and b) excitation 390 nm/emission 420-700 nm compared with c) Epicocconone with SDS and aniline, but no acid: excitation 390 nm/emission 420-700 nm.

Figure 30:
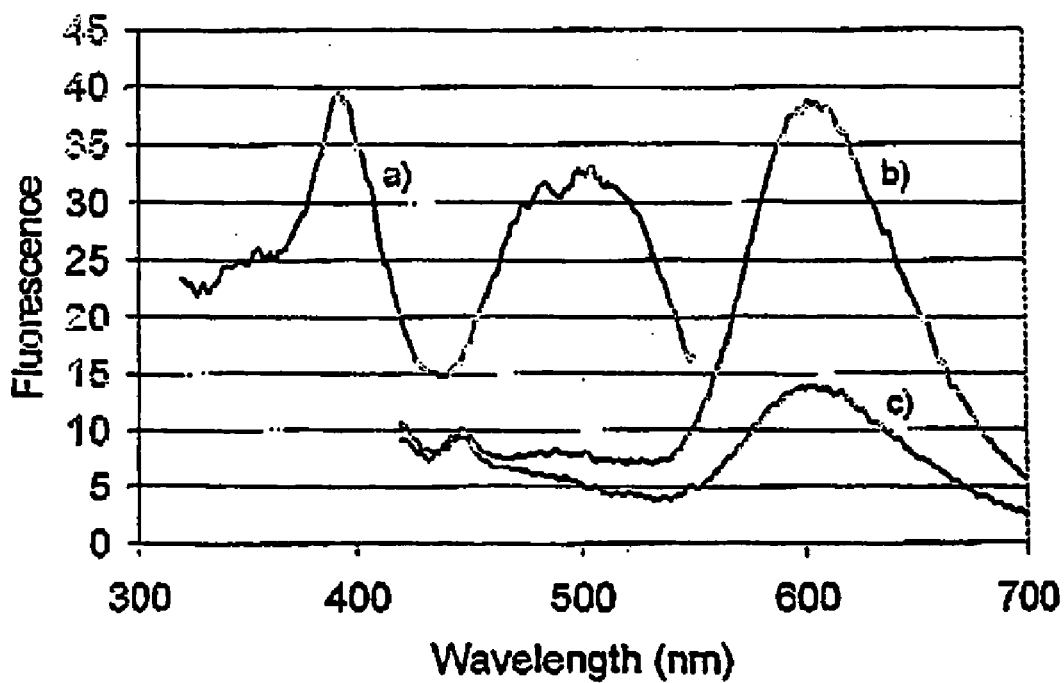

FIG. 30: a) Epicocconone with SDS, acetic acid and TRIS: excitation 320-550 nm/emission 605 nm and b) excitation 390 nm/emission 420-700 nm compared with c) Epicocconone with SDS and TRIS and without acid: excitation 390 nm/emission 420-700 nm.

Figure 31:
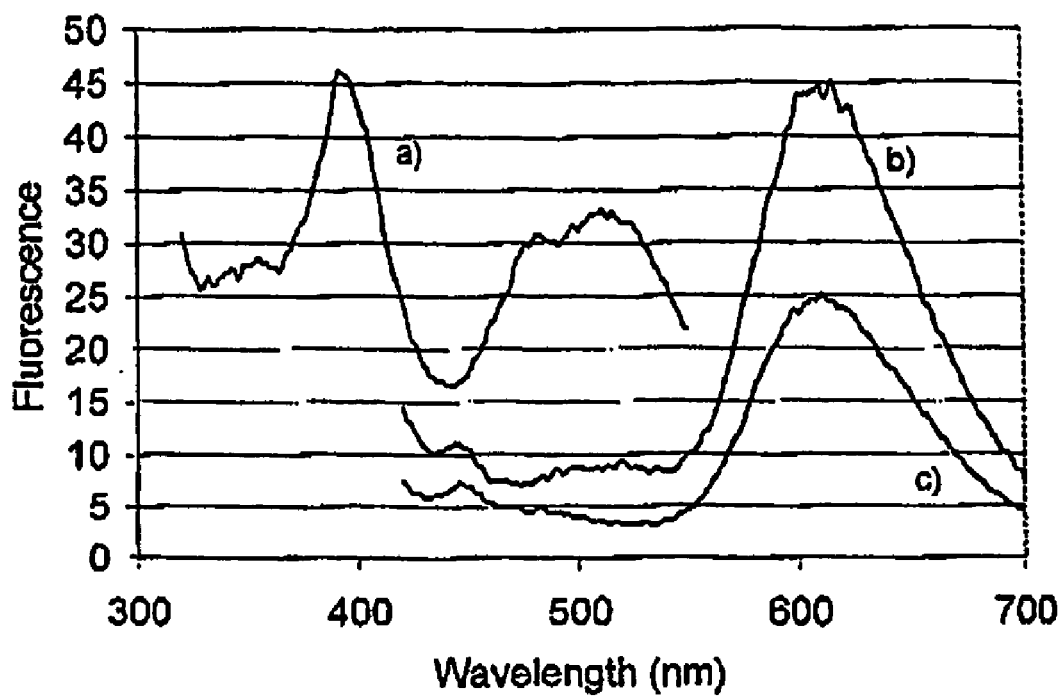

FIG. 31: a) Epicocconone with SDS, acetic acid and ethylamine: excitation 320-550 nm/emission 610 nm and b) excitation 390 nm/emission 420-700 nm compared with c) Epicocconone with SDS and ethylamine and without acid: excitation 390 nm/emission 420-700 nm.

Figure 32:
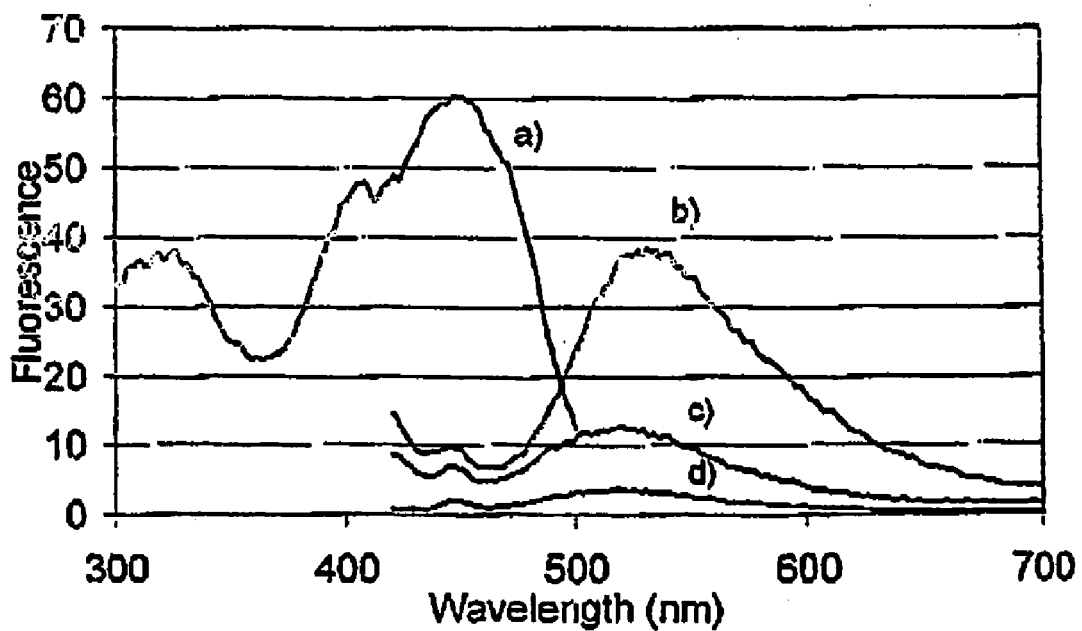

FIG. 32: a) Epicocconone with DTAB, acetic acid and DNA: excitation 300-500 nm/emission 533 nm and b) excitation 390 nm/emission 420-700 nm compared with c) Epicocconone with DTAB and acetic acid and without DNA: excitation 390 nm/emission 420-700 nm and d) Epicocconone alone: excitation 390 nm/emission 420-700 nm.

Figure 33:
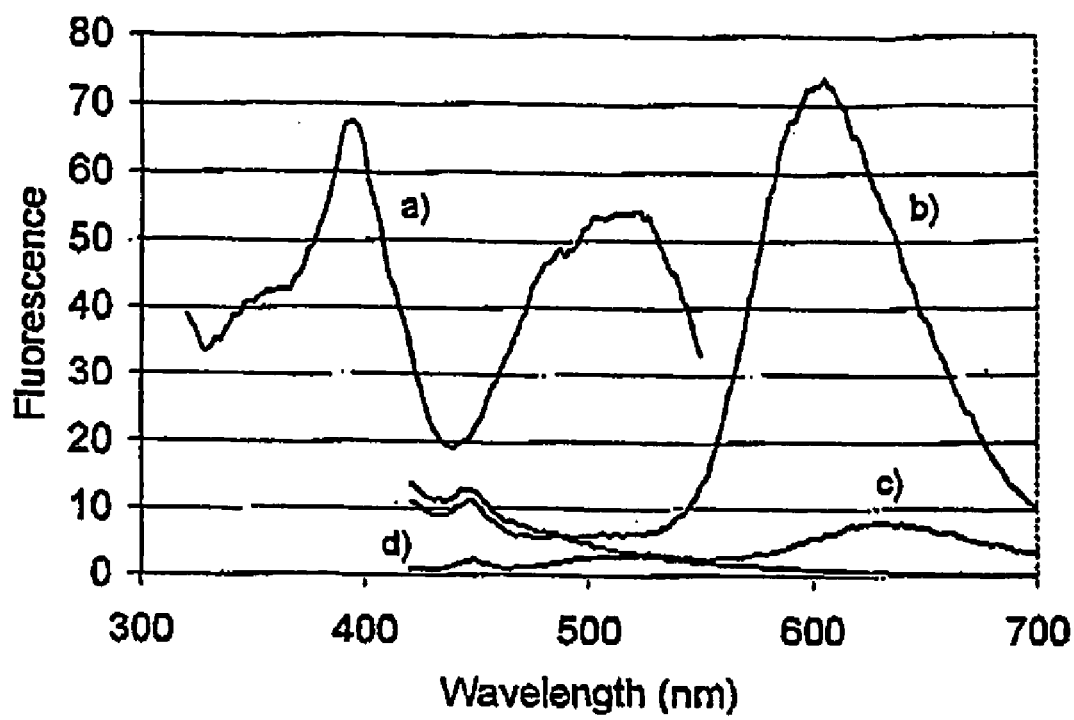

FIG. 33: a) Epicocconone with CHAPS, ammonia and glucosamine hydrochloride: excitation 320-550 nm/emission 605 nm and b) excitation 390 nm/emission 420-700 nm compared with c) Epicocconone with CHAPS and ammonia and without glucosamine hydrochloride: excitation 390 nm/emission 420-700 nm and d) Epicocconone alone: excitation 390 nm/emission 420-700 nm.

Figure 34:
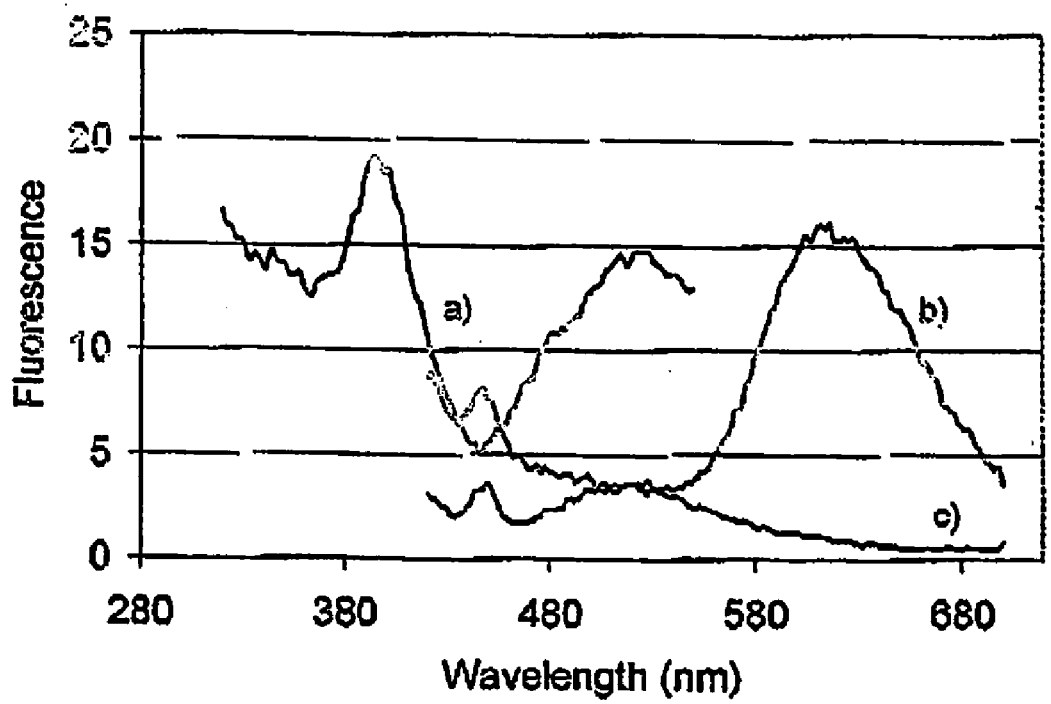

FIG. 34: a) Epicocconone with DTAB and BSA: excitation 320-550 nm/emission 615 nm and b) excitation 390 nm/emission 420-700 nm compared with c) Epicocconone alone: excitation 390 nm/emission 420-700 nm.

Figure 35:
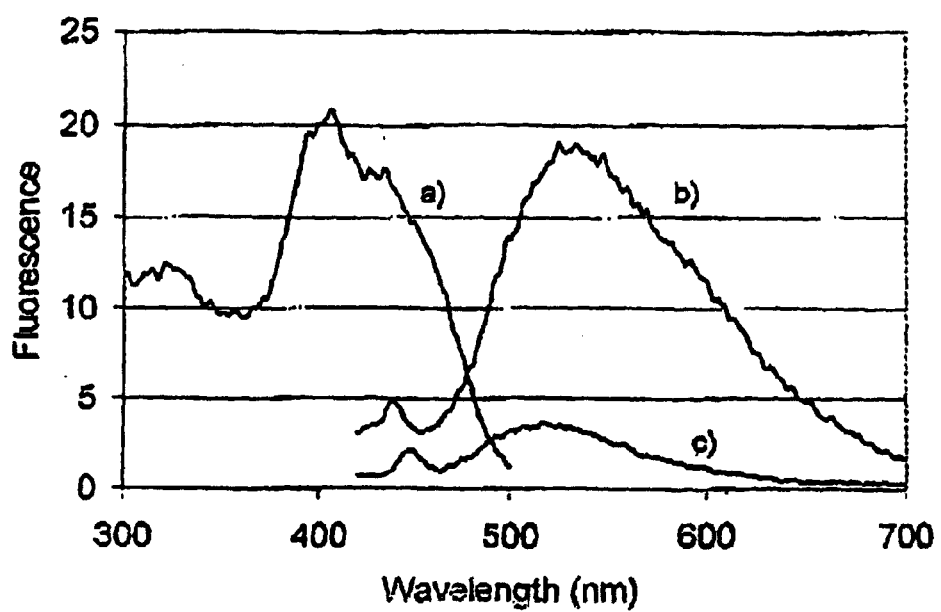

FIG. 35: a) Epicocconone in acetonitrile: excitation 300-500 nm/emission 532 nm and b) excitation 390 nm/emission 420-700 nm compared with c) Epicocconone at the same concentration in water: excitation 390 nm/emission 420-700 nm.

Figure 36:
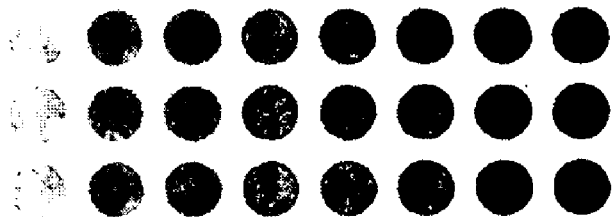

FIG. 36 shows an image of the microtitre plate captured by the Typhoon laser-based imager (532 nm laser, 610 BP 30 emission filter).

Figure 37:
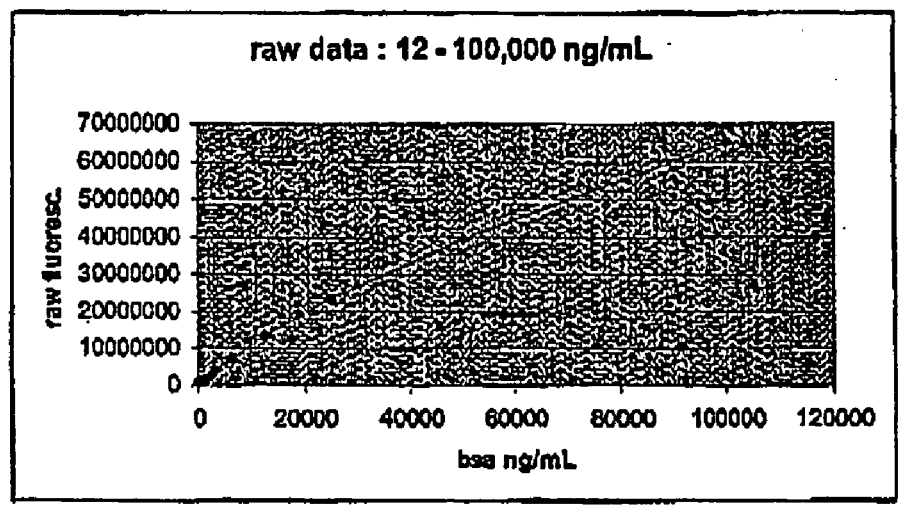
Figure 37:
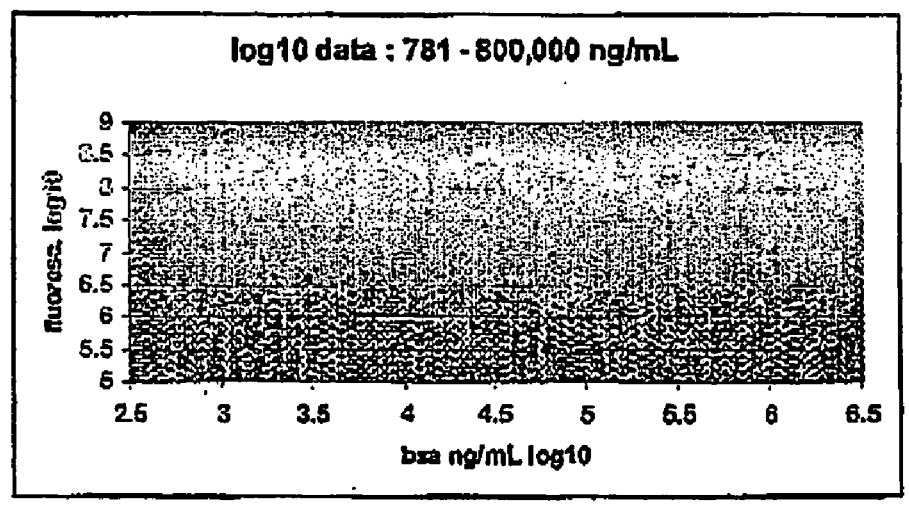

FIG. 37: A) Plot of the raw fluorescence data against BSA concentration per mL in the range of 12 ng-100 µg/mL. The $r^2$ value over the range is 0.985. B) Plot of the $\log_{10}$ of fluorescence data against $\log_{10}$ of BSA concentration per mL in the range of 781 ng-800 µg/mL. The r value over the range is 0.997.

Figure 38:
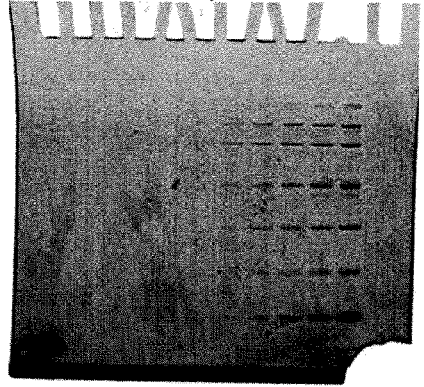
Figure 38:
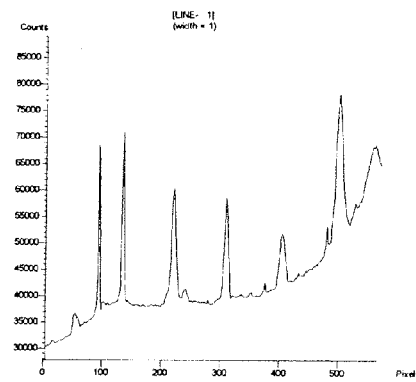
Figure 38:
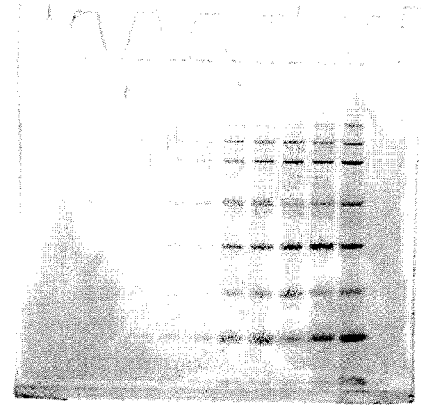
Figure 38:
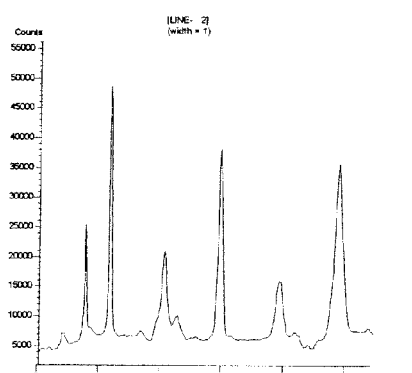
Figure 38:
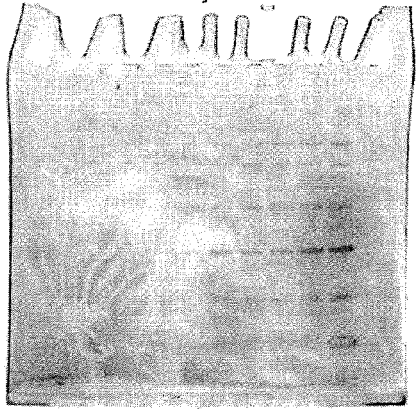
Figure 38:
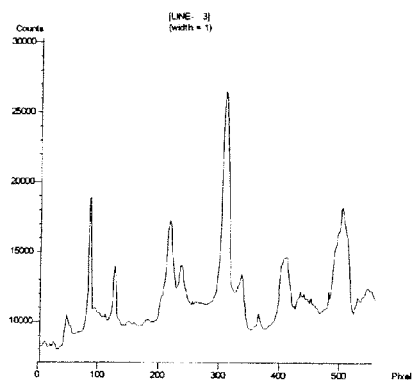
Figure 38:
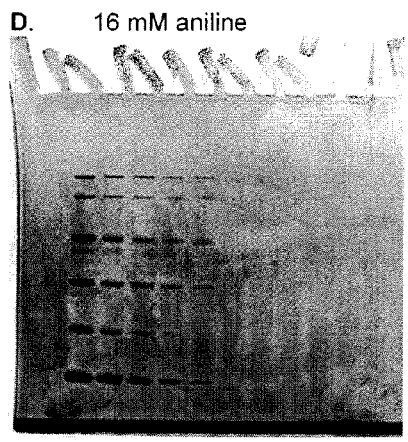
Figure 38:
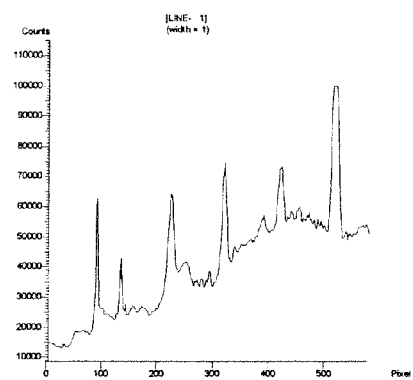
Figure 38:
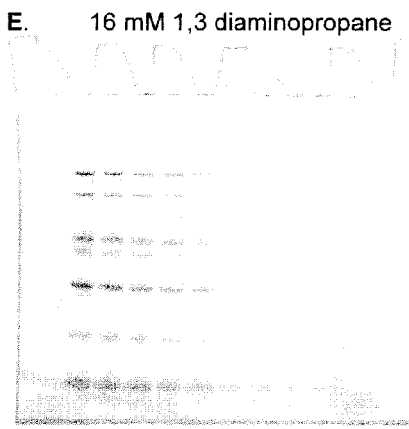
Figure 38:
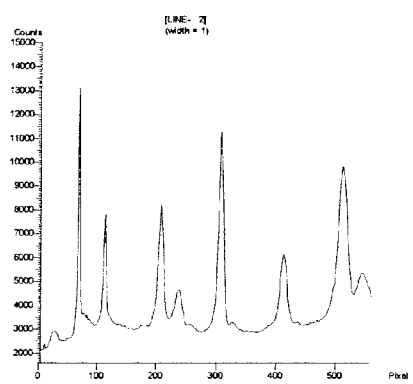
Figure 38:
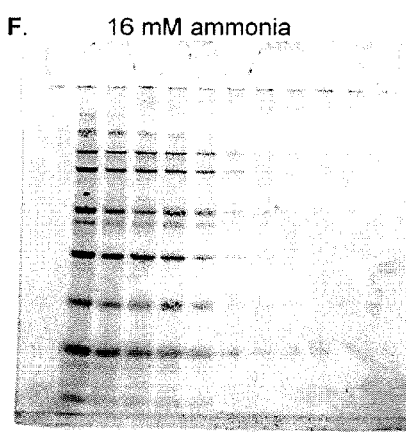
Figure 38:
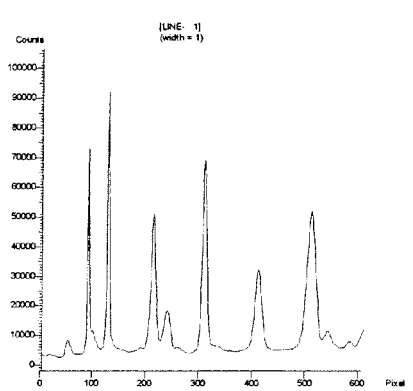
Figure 38:
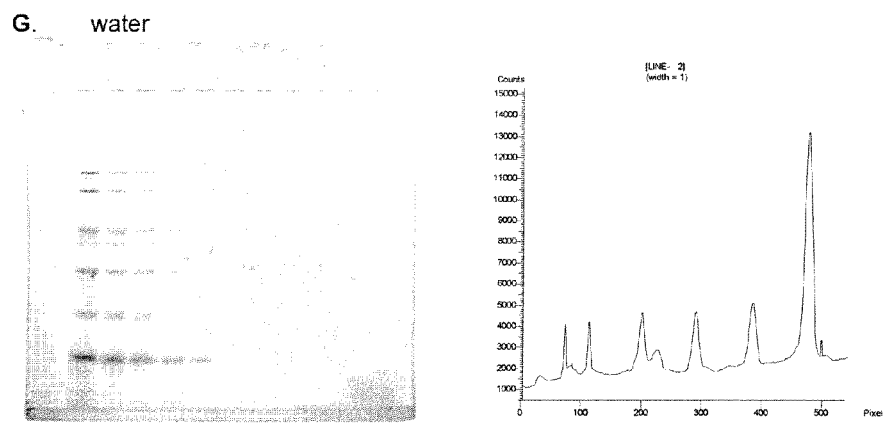

FIG. 38: A-G: Show stained gels and their corresponding intensity traces, following treatment of stained gels with water and different bases.

Figure 39:
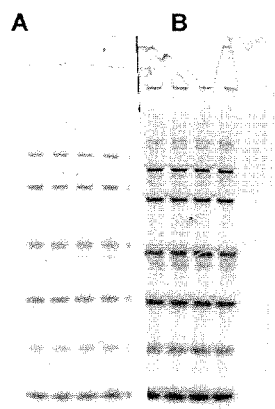

FIG. 39: A and B: Show gel segments following staining with Deep Purple™ and treatment with 8 mM ammonia. Segment 1(A) was stored in 8 mM ammonia under dark conditions for 46 h. Replicate gel segment number 2 (B) was washed 3×10 min. in 8 mM ammonia and transferred to 100 mM orthophosphoric acid and stored under dark conditions also for 46 h.

Figure 40:
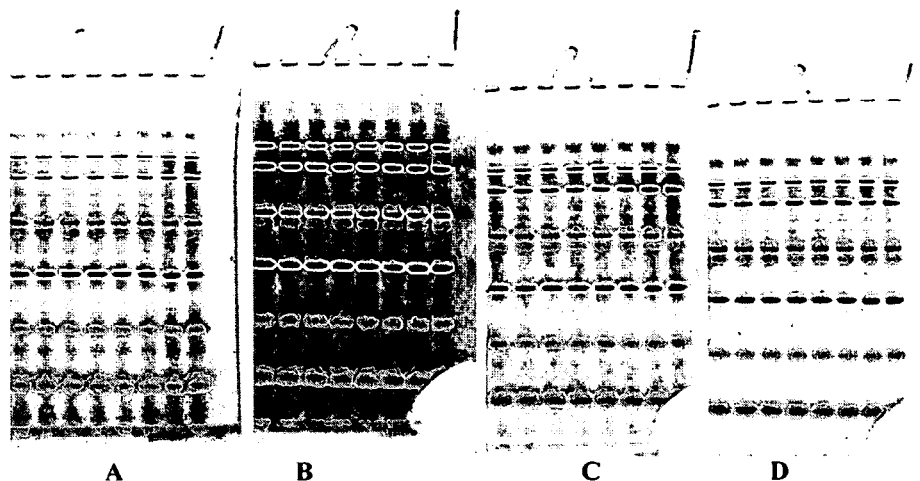
Figure 40:
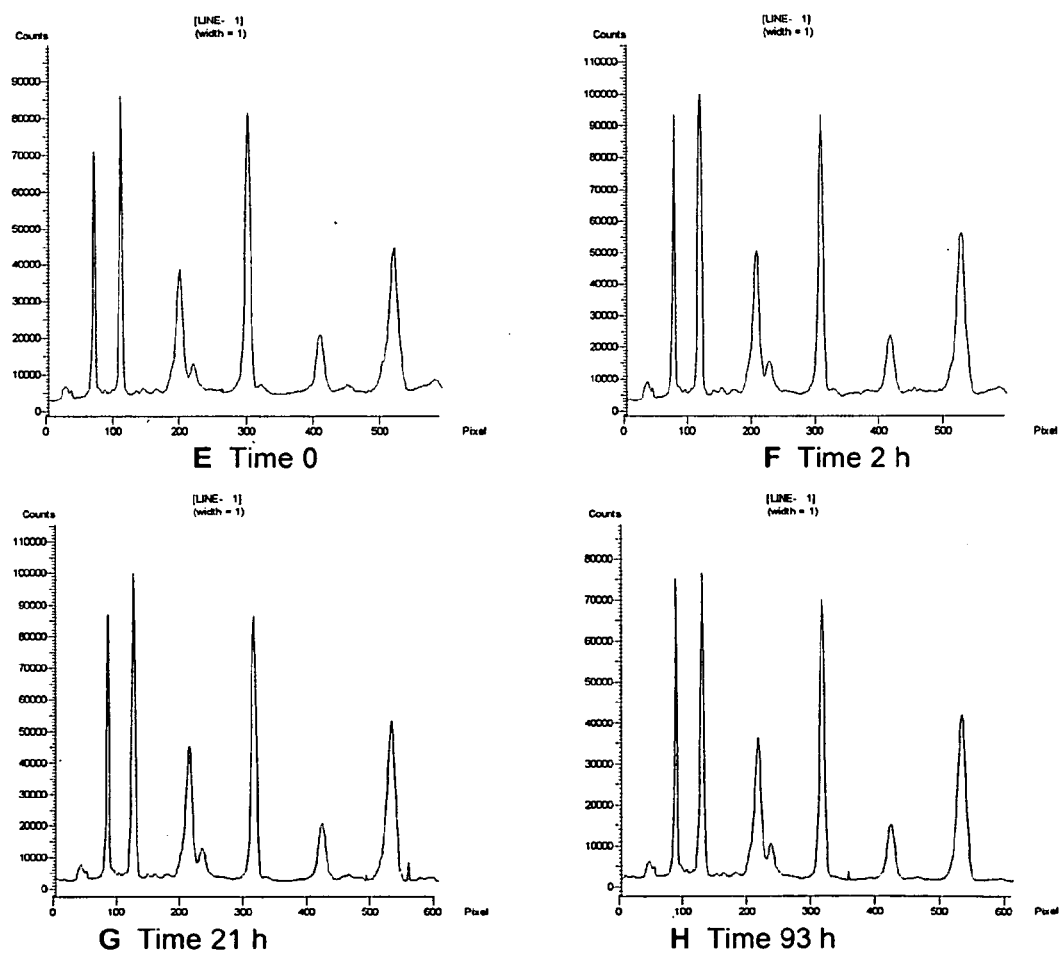

FIG. 40: A-D: gels imaged immediately after treatment with ammonia (A) and following storage in 10 mM sulphuric acid for periods of 2 h (B), 21 h (C) and 93 h(D). E-H: show signal intensity trace of Lane 3 of the gel prior to placing in 10 mM sulfuric acid (E, Time 0) and at 2 h (F), 21 h (G) and 93 h (H) after addition of 10 mM sulfuric acid.

Figure 41:
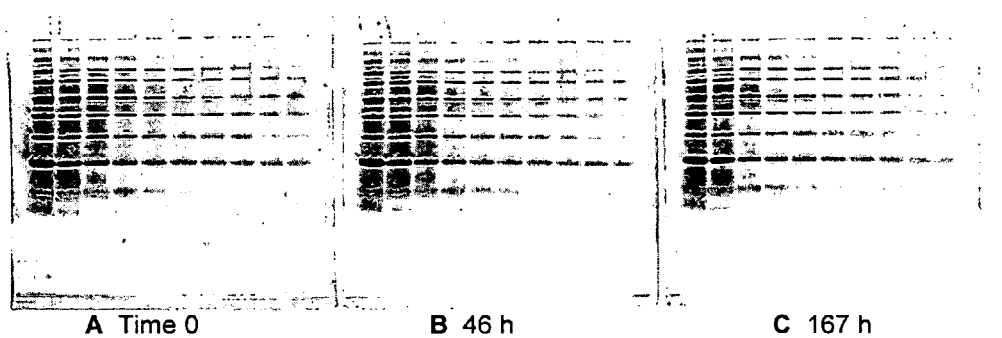

FIG. 41: A-C: gels imaged immediately after treatment with ammonia (A) and following storage in 10 mM acetic acid for periods of 46 h(B) and 167 h (C).

Figure 42:

FIG. 42: Shows Typhoon-scanned images of the DNA gel strips (1: No detergent treatment, Epicocconone staining only; 2: SDS-incubation and Epicocconone staining; 3: DDTAB-incubation and Epicocconone staining; 4: SDS and DDTAB-incubation, and Epicocconone staining).

Figure 43:

FIG. 43: Typhoon image of red emission light. 532 nm laser, 560 LP filter. After addition of stain, 10 mM ammonia solution added to wells after addition of Deep Purple™ formulated as described in Protocol.

Figure 44:
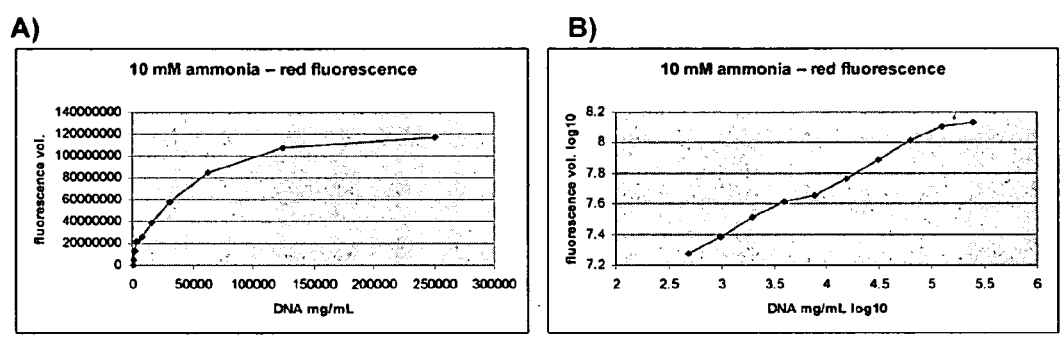

FIG. 44: A) Signal from FIG. 43 plotted as raw data. B) plot of the $\log_{10}$ transformed data.

Figure 45:

FIG. 45: Typhoon image of green emission light. 532 nm laser, 526 SP filter. After addition of stain, 10 mM acetic acid solution added to wells after addition of Deep Purple™ formulated as described in Protocol.

Figure 46:
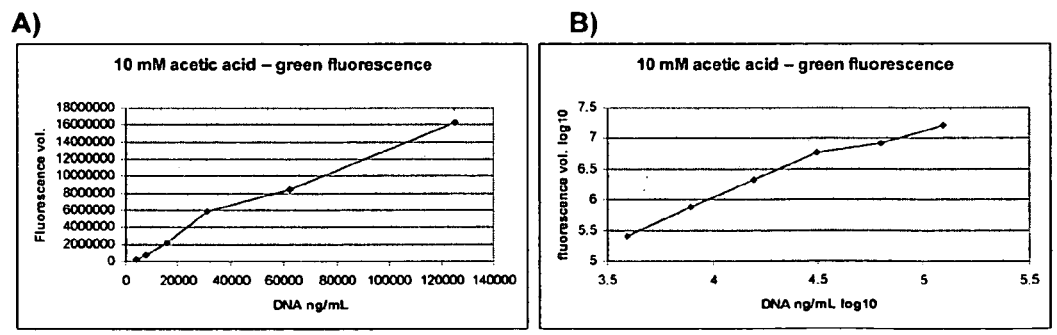

FIG. 46: A) Signal from FIG. 45 plotted as raw data. B) plot of the same data transformed $\log_{10}$.

Figure 47:
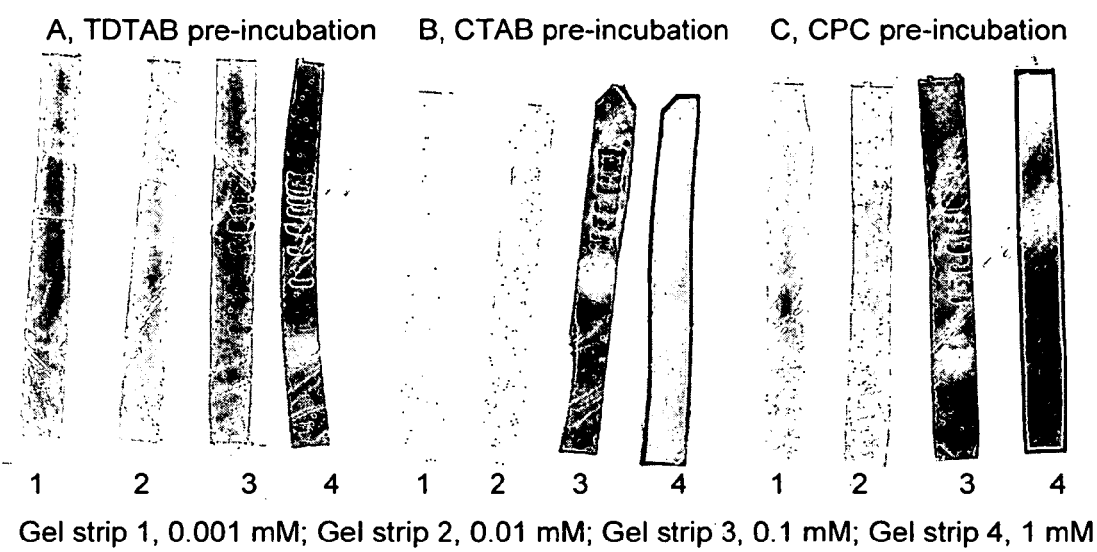

FIG. 47: shows Typhoon-scanned images of the DNA gel (A and C, DNA MWM XVII; B, SPP-1 DNA/Eco RI) strips. FIG. 47-A, the DNA gel strips that were pre-incubated in TDTAB (1, 0.001 mM; 2, 0.01 mM, 0.1 mM and 1 mM) before epicocconone staining; FIG. 47-B, the DNA gel strips that were pre-incubated in CTAB (1, 0.001 mM; 2, 0.01 mM, 0.1 mM and 1 mM) before epicocconone staining; FIG. 47-C, the DNA gel strips that were pre-incubated in CPC (1, 0.001 mM; 2, 0.01 mM, 0.1 mM and 1 mM) before epicocconone staining.

The invention will now be described with reference to non-limiting Examples.

EXAMPLES

Example 1

Effect Bases, Acids and Detergents on Fluorescence of Epicocconone

To illustrate the enhancement and an increase in the Stokes' shift when epicocconone is in the presence of an amine, fluorescence measurements were recorded in solution of epicocconone with a variety of amines, acids and detergents. It was found that a combination of an amine and a detergent enhances the fluorescence and causes an increase in the Stokes' shift. Inorganic base such as $NaHCO_3$ caused a loss of fluorescence and the addition of a detergent did not recover the fluorescence.

Fluorescence spectroscopy was carried out using a Perkin Elmer LS 50B Luminescence Spectrometer (Perkin Elmer, Melbourne Australia). Freshly prepared solutions were placed into a Hellma Quartz SUPRASIL precision cell and the cell was then placed into the spectrometer. Typically a solution was 3 mL in volume and the components were added using a Gilson M-1000 Microman positive displacement pipette. The components and their final concentrations are given for each sample. All solutions are in water (Millipore RiOS 5) unless otherwise stated.

Definitions and Sources

Deep Purple™ (Amersham Biosciences, Australia, Cat. Nos. RPN6305 or RPN6306) is a partially purified form of epicocconone. It has an absorbance at 550 nm of 0.8. An aqueous stock solution was prepared from the methanol stock solution by diluting it by a factor of 12.5 with water. Final solutions in the quartz cell are diluted further by a factor of 4. The total dilution of the Deep Purple™ stock solution in methanol is 1 in 50. (Deep Purple™ from Amersham in methanol)

Epicocconone was isolated by the method described in Bell PJL and Karuso P[13], incorporated herein by reference. A stock solution of epicocconone was prepared in DMSO (28 μg/mL or 42 μg/mL in DMSO) and this was used to prepare stock solutions in water by diluting the DMSO solution by a factor of 5 or 10 respectively. Final solutions in the quartz cell are diluted further by a factor of 4. Final concentrations of epicocconone are reported with each example.

Acetic acid: (APS, Asia Pacific Specialty Chemicals Ltd, formerly Ajax: 1-2.5L GL)
Acetonitrile: (Ajax Finechem-2315-2.5L GL)
Ammonia solution: (Ajax Finechem-43-2.5L GL)
Aniline: (Aldrich-13,293-4)
Benzylamine: (BDH-27355)
BSA—Bovine serum albumin: (Sigma-A-2153)
Butylamine: (Aldrich-47,130-5)
CHAPS-3-[(3-Cholamidopropyl)dimethylammonio]-1-propanesulfate: (BDH-30632)
Cholic acid sodium salt: (Sigma-C-1254)
CPC—Cetylpyridimium chloride: (Ajax-UL 0000145)
CTAB—Cetyltrimethylammonium bromide: (Sigma-H-5882)
1,3-Diaminopropane: (Koch-Light Laboratories-4774)
DMSO—Dimethyl sulfoxide: (Aldrich-27,043-1)
DNA—Deoxyribonucleic acid sodium salt is from Salmon testes: (Sigma-D-1626)
DTAB—Dodecyltrimethylammonium bromide: (Sigma-D-8638)
TDTAB—Tetradecyltrimethylammonium bromide (Sigma-T-4762)
Ethylamine: (Lancaster-10838)
D-(+)-Glucosamine hydrochloride: (Sigma-G-4875)
$H_2SO_4$—Sulfuric acid: (Ajax Finechem-534)
Octylamine: (Lancaster-8.06917.0250)
Octyl-D-glucoside: (ICN Biomedicals-153941)
SDS—Sodium dodecylsulfate: (BDH-301754)
TRIS (HCl)—Tris(hydroxymethyl)aminomethane hydrochloride salt: (Sigma-T-3253)
Triton X-100: (BDH-30632)
Tween 20—Polyoxyethylenesorbitan monolaurate: (Sigma-P-1379)
Tween 80—Polyoxyethylenesorbitan monooleate: (BDH-56023)

The concentrations of the detergents other than SDS were such that they were above their respective CMC values Stock concentrations of detergents used:

| | |
|---|---|
| CHAPS: | 0.27% w/v |
| Cholic acid sodium salt: | 1.7% w/v (40 mM) |
| CPC: | 0.148% w/v (4.1 mM) |
| CTAB: | 0.172% w/v (4.7 mM) |
| DTAB: | 0.2% w/v (6.5 mM) |
| Octyl-D-glucoside: | 3.1% w/v (106 mM) |
| SDS: | 1.2% w/v (41.7 mM) |
| Triton ® X-100: | 0.27% w/v (4.35 mM) |
| Tween 20: | 0.56 w/v |
| Tween 80: | 0.64% w/v |

The detergents are diluted 1 in 4 in the final solution.

(i) Enhancing the Fluorescence of Epicocconone and Deep Purple™ by Acids

Figure 1:
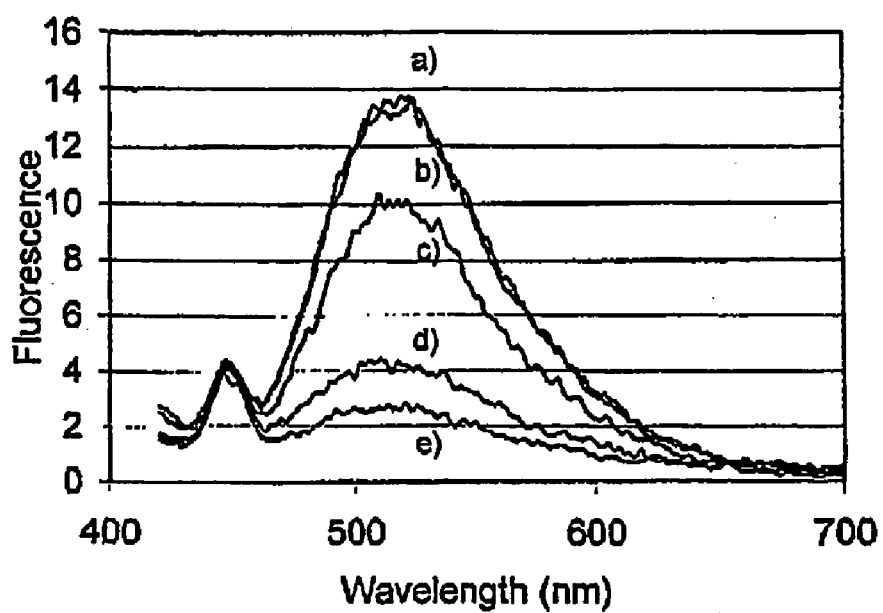
FIG. 1 shows the emission profile of epicocconone when excited at 390 nm with a) 100 mM aqueous acetic acid, b) 1 mM acetic acid, c) 10 µM acetic acid, d) 1 µM acetic acid and e) no acetic acid.

The fluorescence of epicocconone in water can be enhanced by the addition of acetic acid (see FIG. 1). Using a fixed concentration of epicocconone (1.05 μg/mL; $2.56 \times 10^{-6}$ M) in water fluorescence spectra were recorded with final acetic acid concentrations ranging from 100 nM to 100 mM.

Figure 2:
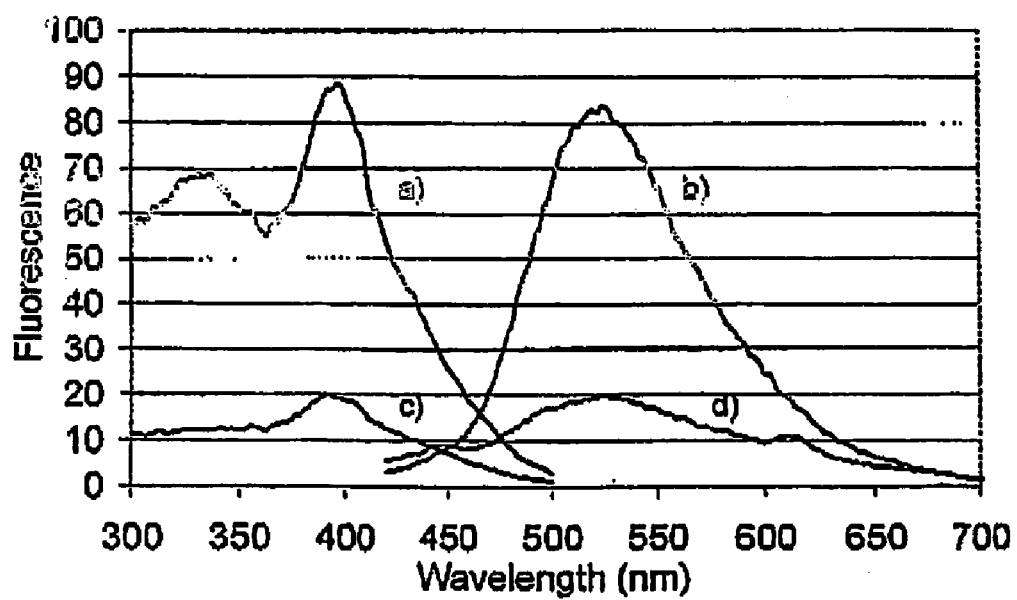
FIG. 2: a) Deep Purple™ with 1 mM acetic acid: excitation 300-500 nm/emission 524 nm and b) excitation 390 nm/emission 420-700 nm compared with c) Deep Purple™ at the same concentration without acid: excitation 300-500 nm/emission 523 nm and d) excitation 390 nm/emission 420-700 nm.

FIG. 2 shows that the fluorescence of Deep Purple in water can also be enhanced by the addition of acetic acid.

Figure 3:
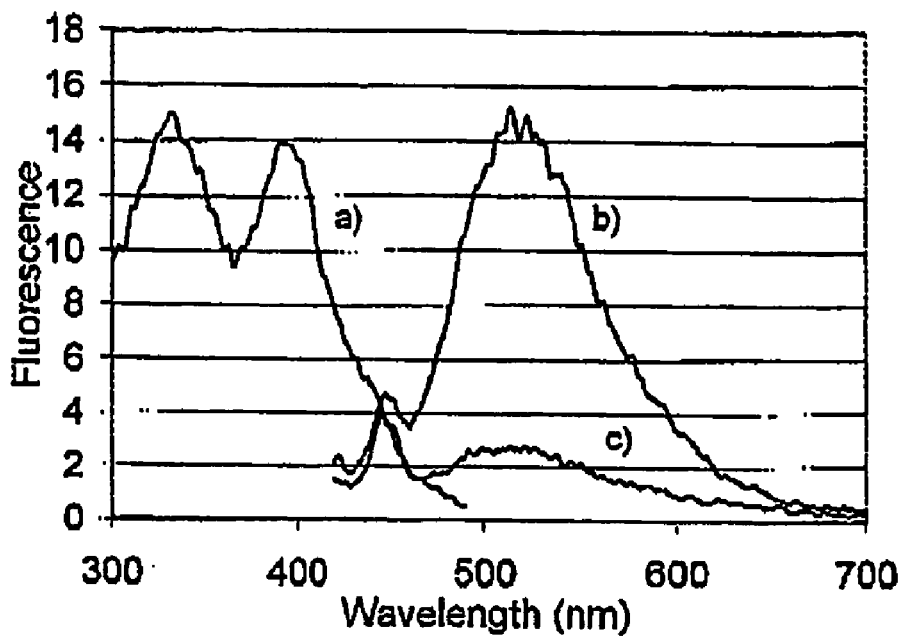
FIG. 3: a) Epicocconone with 1 mM $H_2SO_4$: excitation 300-490 nm/emission 516 nm and b) excitation 390 nm/emission 420-700 nm compared with c) Epicocconone without acid: excitation 390 nm/emission 420-700 nm.

The fluorescence of epicocconone in water can also be enhanced by the addition of other acids such as for example sulfuric acid. The fluorescence spectra shown in FIG. 3 is with a fixed concentration of epicocconone (1.05 μg/mL; $2.56 \times 10^{-6}$ M) in water and a final concentration of 1 mM $H_2SO_4$.

(ii) Enhancing the Fluorescence of Epicocconone and Deep Purple™ by Detergents

The fluorescence of epicocconone in water can be enhanced by the addition of SDS (anionic detergent). Increasing the SDS concentration increases the fluorescence observed (exciting at 390 nm, emission maximum at 525 nm).

Figure 4:
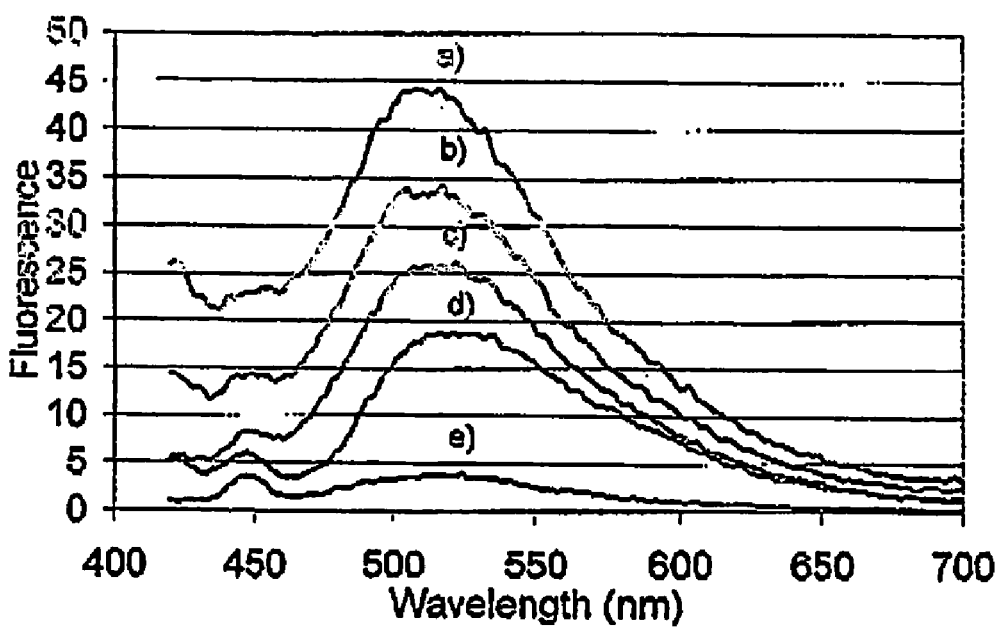
FIG. 4: The emission profile of epicocconone when excited at 390 nm with a) 1.8% aqueous SDS (w/v), b) 0.8% SDS, c) 0.4% SDS, d) 0.1% SDS and e) 0.1% SDS.

Using a fixed concentration of epicocconone (1.05 μg/mL; $2.56 \times 10^{-6}$ M) in water fluorescence spectra were recorded with final concentrations of SDS ranging from 0.1% to 1.8% (w/v). The fluorescence spectra in FIG. 4 show that fluorescence increases with increasing SDS concentration.

Figure 5:
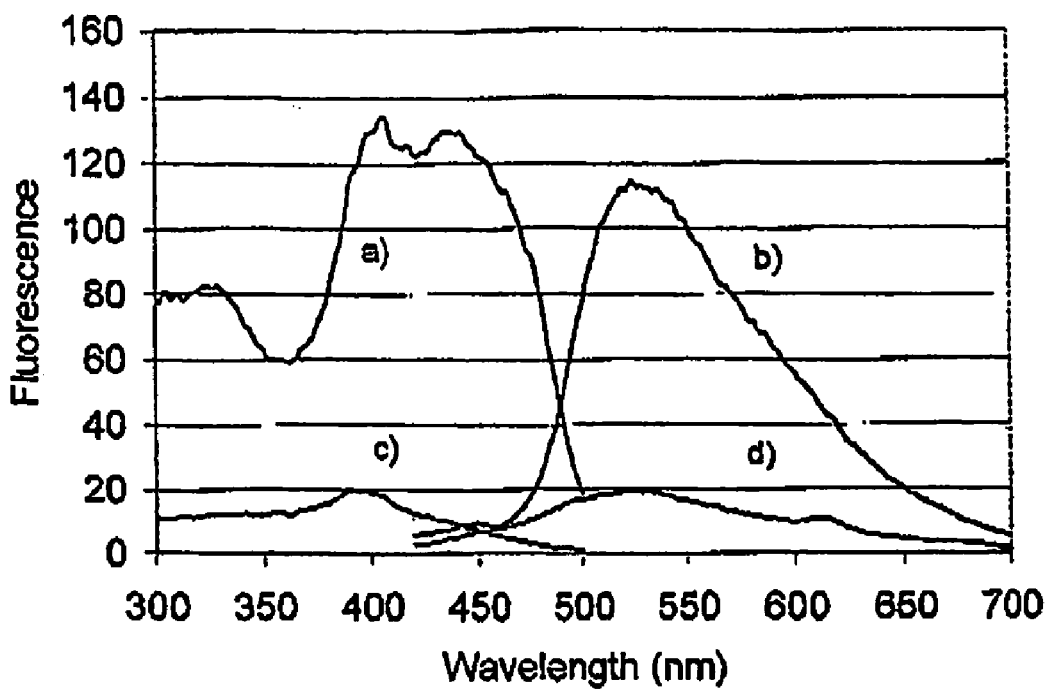
FIG. 5: a) Deep Purple™ with 0.3% aqueous SDS (w/v): excitation 300-500 nm/emission 525 nm and b) excitation 390 nm/emission 420-700 nm compared with c) Deep Purple™ at the same concentration without SDS: excitation 300-500 nm/emission 523 nm and d) excitation 390 nm/emission 420-700 nm.

The fluorescence of Deep Purple in water can also be enhanced by the addition of SDS (see FIG. 5).

Figure 6:
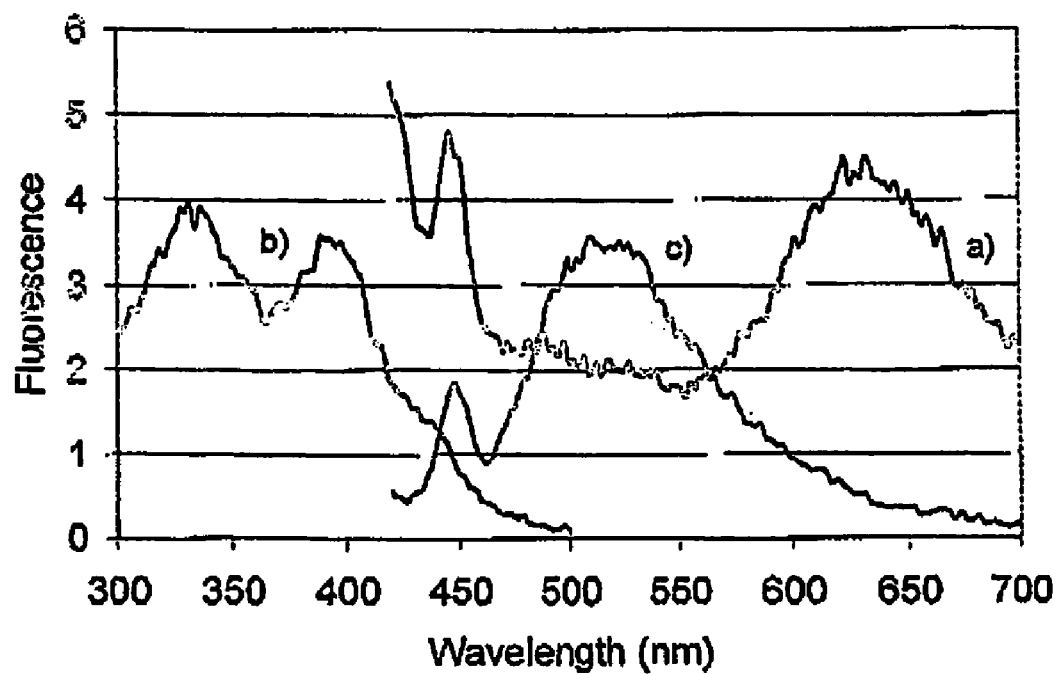
FIG. 6: a) Epicocconone with CTAB: excitation 390 nm/emission 420-700 nm compared with b) the same concentration of epicocconone without CTAB: excitation 300-500 nm/emission 516 nm and c) excitation 390 nm/emission 420-700 nm.

The fluorescence of epicocconone in water can be enhanced by the addition of other detergents such as for example CTAB (cationic detergent) with an accompanying increase in Stokes' shift. The addition of CTAB to an epicocconone solution shows an increase in fluorescence at 625 nm with respect to epicocconone alone at 625 nm. There is a decrease in fluorescence at 525 nm when CTAB is added. The fluorescence spectra shown in FIG. 6 were generated with concentrations of epicocconone of 1.05 μg/mL, ($2.56 \times 10^{-6}$ M) in water and a final concentration of CTAB of 1.175 mM.

Figure 7:
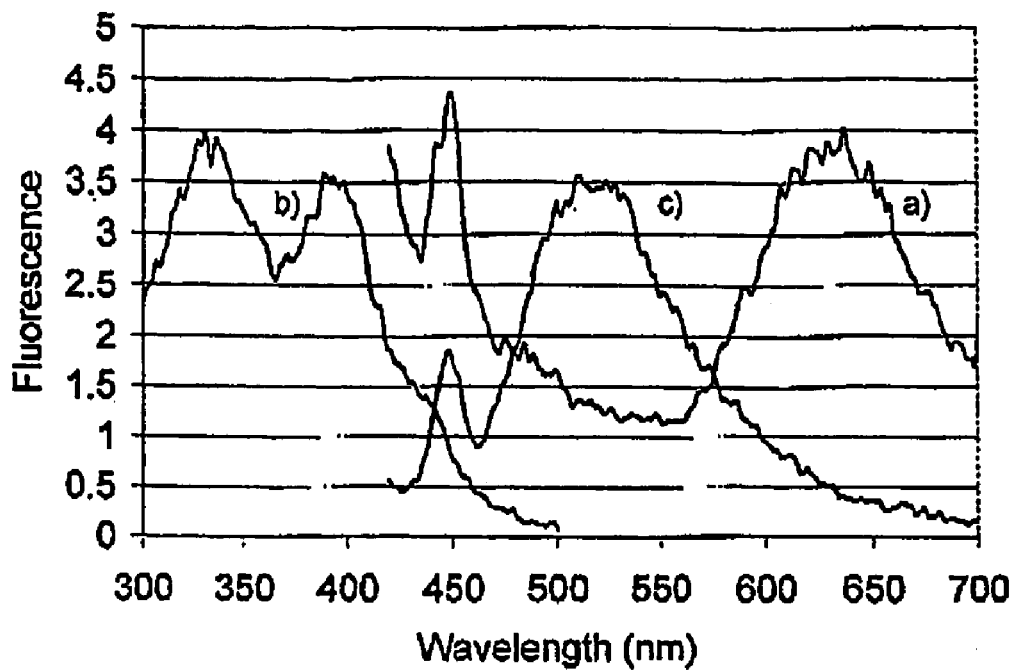
FIG. 7: a) Epicocconone with CPC: excitation 390 nm/emission 420-700 nm compared with b) Epicocconone at the same concentration without CPC: excitation 300-500 nm/emission 516 nm and c) excitation 390 nm/emission 420-700 nm

The effect observed with CTAB is also seen with other detergents, eg CPC. The fluorescence of epicocconone in water can be enhanced by the addition of CPC (cationic detergent) with an accompanying Stokes' shift. The addition of CPC to a solution of epicocconone increases its fluorescence at 630 nm with respect to epicocconone alone at 630 nm. There is a decrease in fluorescence at 520 nm when CPC is added. The fluorescence spectra shown in FIG. 7 were generated with concentrations of epicocconone of 1.05 µg/mL ($2.56 \times 10^{-6}$ M) and a final concentration of CPC of 1.025 mM.

Figure 8:
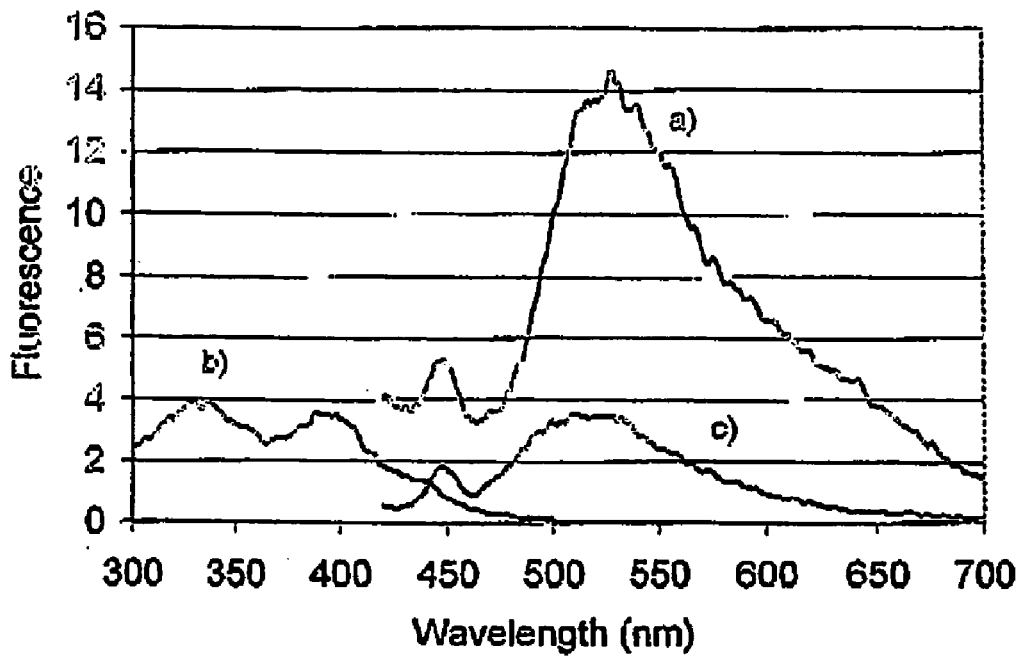
FIG. 8: a) Epicocconone with CHAPS: excitation 390 nm/emission 420-700 nm compared with b) Epicocconone at the same concentration without CHAPS: excitation 300-500 nm/emission 516 nm and c) excitation 390 nm/emission 420-700 nm.

The fluorescence of epicocconone in water can also be enhanced by the addition of CHAPS (zwitterionic detergent). The fluorescence spectra shown in FIG. 8 were generated with concentrations of epicocconone of 1.05 µg/mL ($2.56 \times 10$ M) in water and a final concentration of CHAPS of 0.0675% (w/v).

The fluorescence of epicocconone in water can also be enhanced by the addition of a number of different non-ionic detergents (see list of detergents set out below). The fluorescence spectra shown in FIG. 12-15 were generated with concentrations of epicocconone of 1.05 µg/mL ($2.56 \times 10^{-6}$ M) in water.

Figure 9:
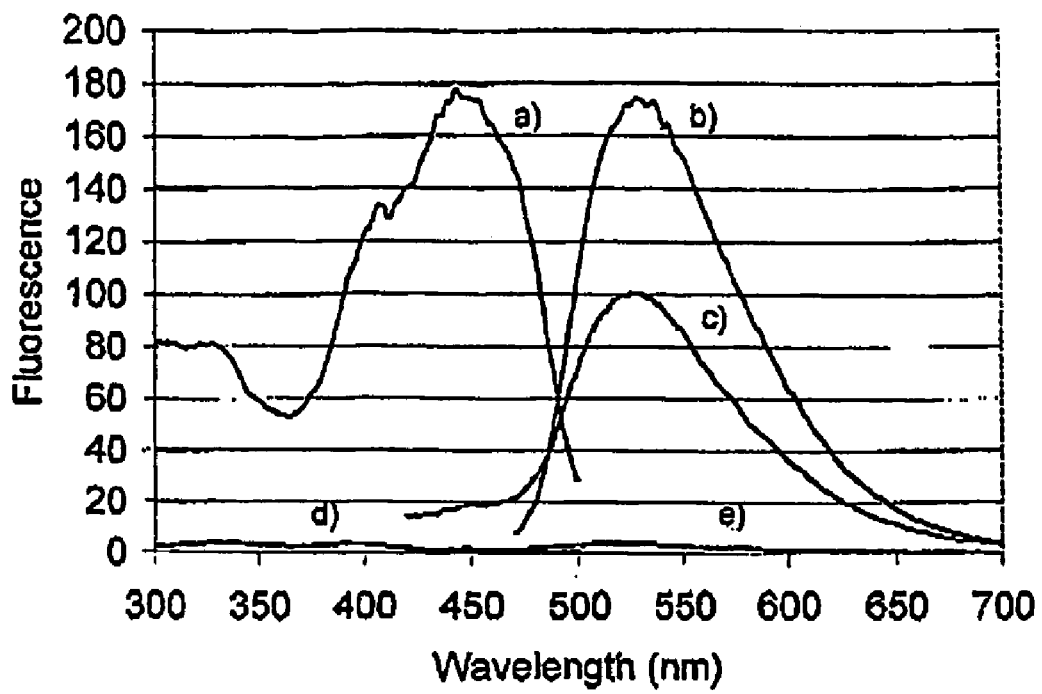
FIG. 9: a) Epicocconone with Tween 80: excitation 300-500 nm/emission 526 nm, b) excitation 440 nm/emission 470-700 nm and c) excitation 390 nm/emission 420-700 nm compared with d) Epicocconone at the same concentration without Tween 80: excitation 300-500 nm/emission 516 nm and E) excitation 390 nm/emission 420-700 nm.
Figure 10:
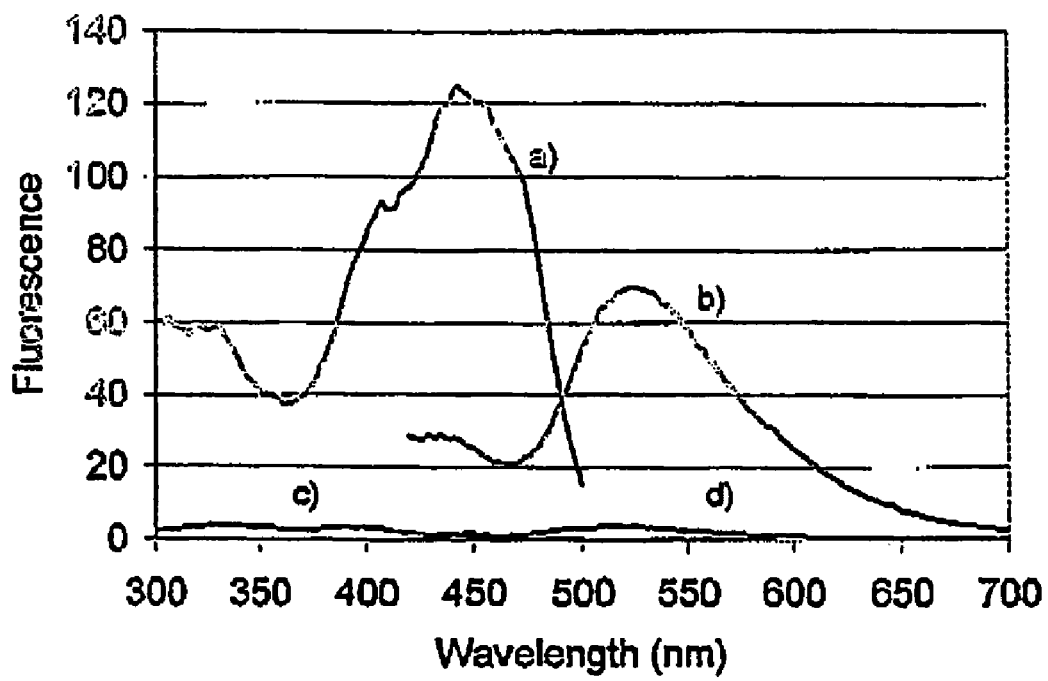
FIG. 10: a) Epicocconone with Tween 20: excitation 300-500 nm/emission 524 nm and b) excitation 390 nm/emission 420-700 nm compared with c) Epicocconone at the same concentration without Tween 20: excitation 300-500 nm/emission 516 nm and d) excitation 390 nm/emission 420-700 nm.
Figure 11:
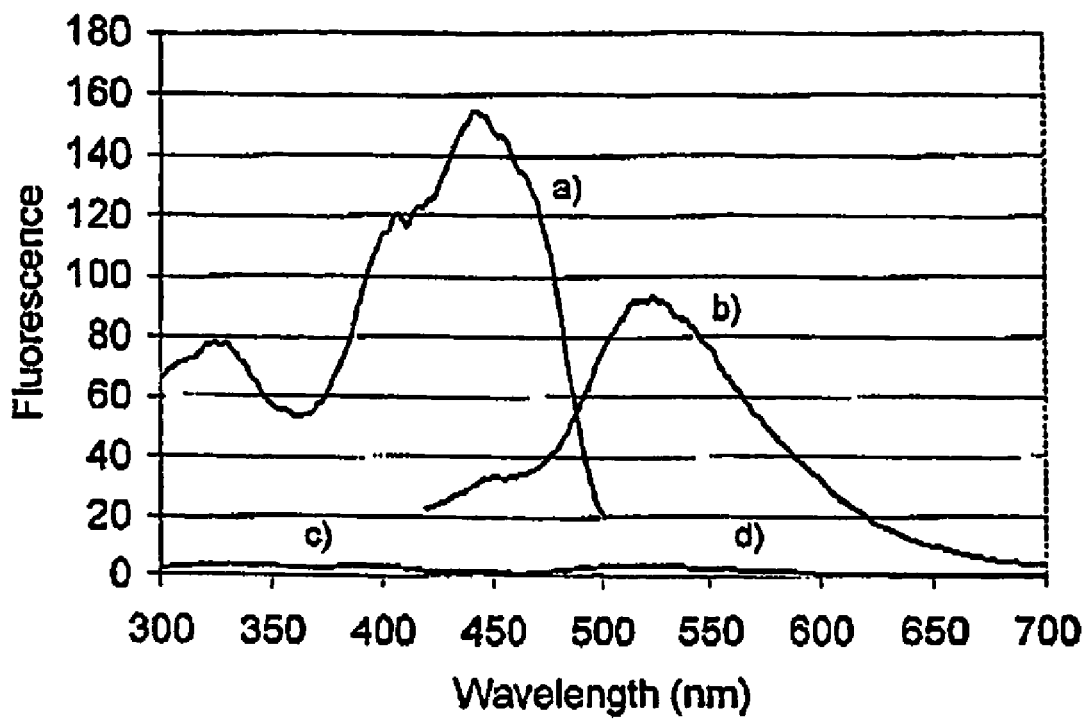
FIG. 11: a) Epicocconone with octyl D-glucoside: excitation 300-500 nm/emission 524 nm and b) excitation 390 nm/emission 420-700 nm compared with c) Epicocconone at the same concentration without octyl D-glucoside: excitation 300-500 nm/emission 516 nm and d) excitation 390 nm/emission 420-700 nm.
Figure 12:
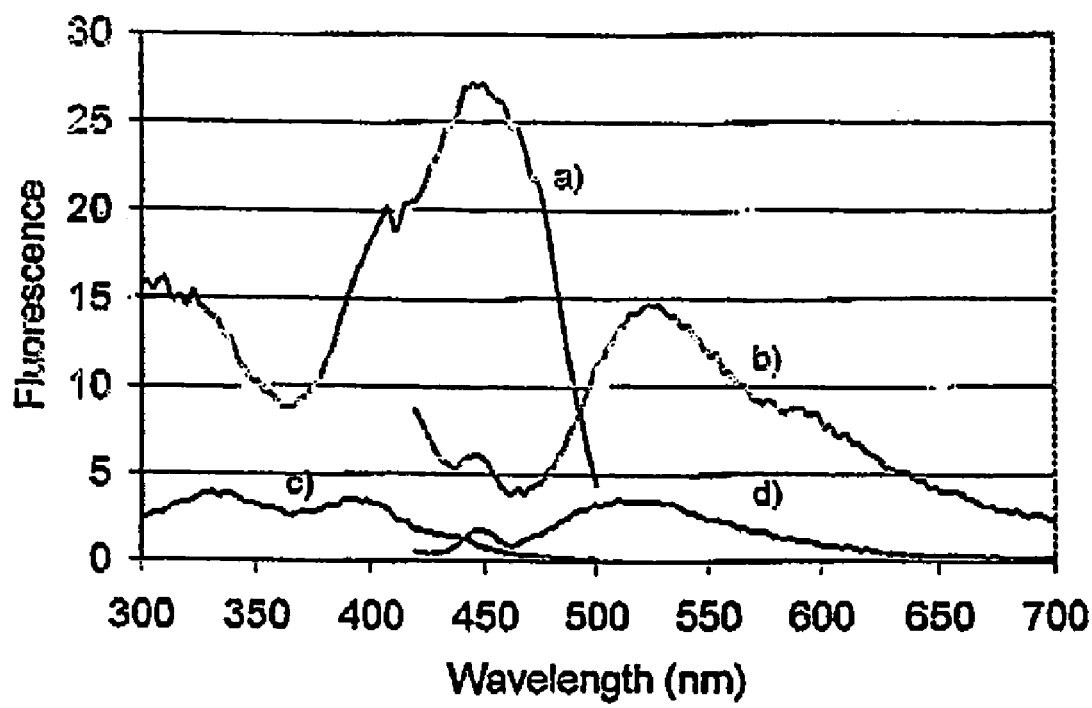
FIG. 12: a) Epicocconone with Triton X-100: excitation 300-500 nm/emission 526 nm and b) excitation 390 nm/emission 420-700 nm compared with c) Epicocconone at the same concentration without Triton X-100: excitation 300-500 nm/emission 516 nm and d) excitation 390 nm/emission 420-700 nm.

Tween 80 (final concentration of 0.16% w/v)—FIG. 9
Tween 20 (final concentration of 0.14% w/v)—FIG. 10
Octyl-D-glucoside (final concentration of 0.775% w/v)—FIG. 11
Triton X-100 (final concentration of 0.0675% w/v)—FIG. 12

(iii) Enhancing the Fluorescence of Epicocconone and Deep Purple™ by Detergents and Acids The fluorescence of epicocconone in water can also be enhanced by the addition of acid and a number of different detergents (see list of detergents set out below). The fluorescence spectra shown in FIG. 14-17 were generated with concentrations of epicocconone of 1.1.4 µg/mL ($3.4 \times 10^{-6}$ M) in water and a final concentration of acetic acid of 1 mM.

Figure 13:
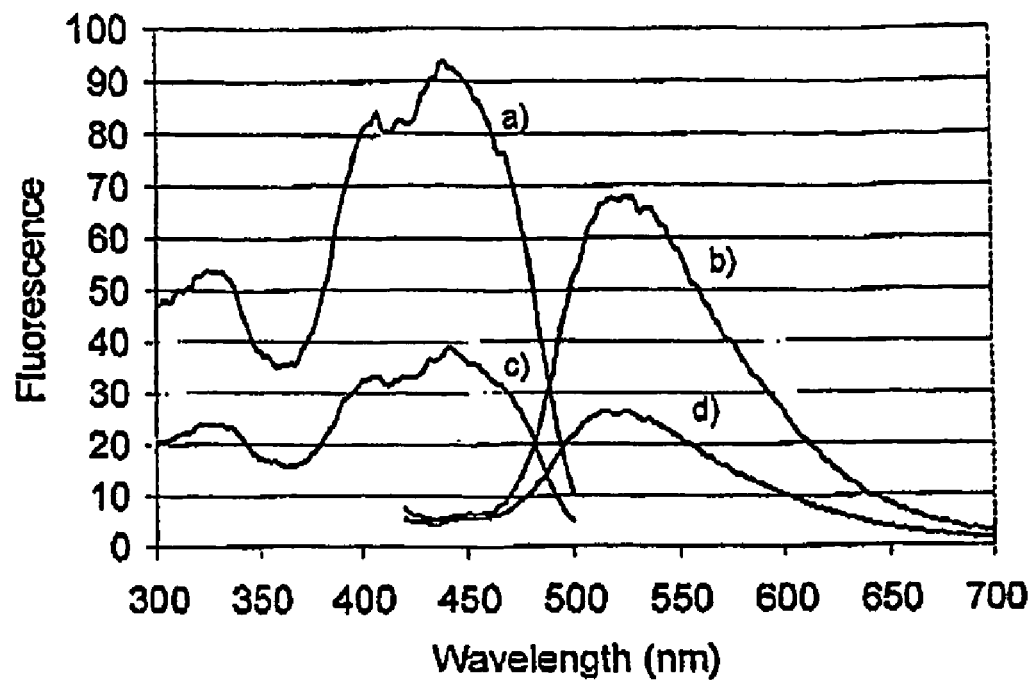
FIG. 13: a) Epicocconone with SDS and acetic acid: excitation 300-500 nm/emission 525 nm and b) excitation 390 nm/emission 420-700 nm compared with c) Epicocconone with SDS, but no acid: excitation 300-500 nm/emission 515 nm and d) excitation 390 nm/emission 420-700 nm.
Figure 14:
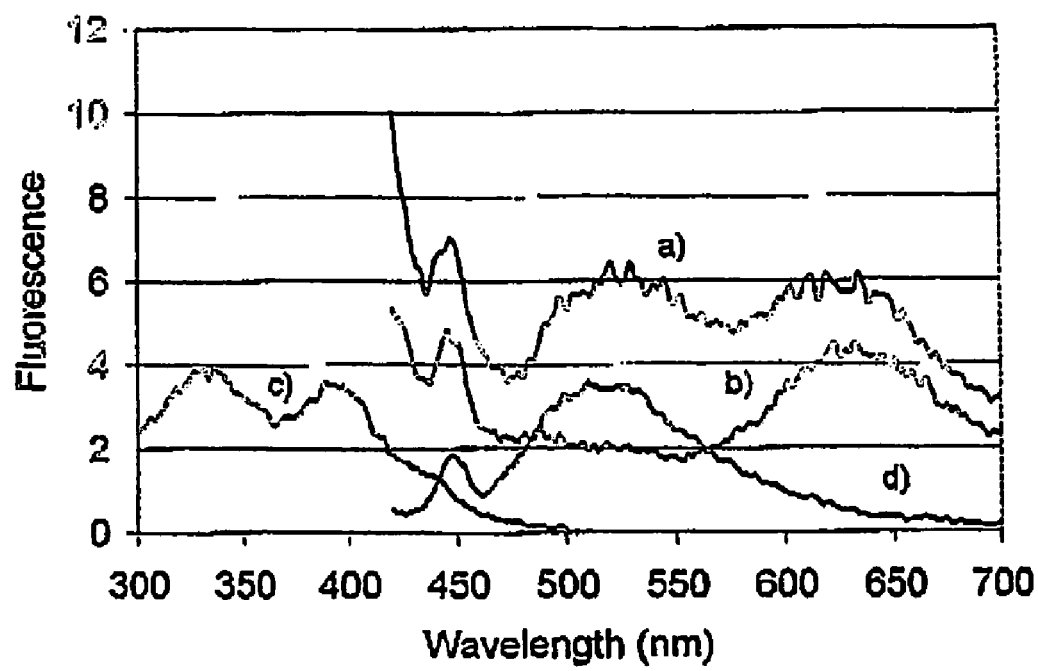
FIG. 14: a) Epicocconone with CTAB and acetic acid: excitation 300-500 nm/emission 516 nm compared with b) Epicocconone with CTAB, but without acid: excitation 390 nm/emission 420-700 nm and c) Epicocconone at the same concentration without CTAB and without acid: excitation 300-500 nm/emission 516 nm and d) excitation 390 nm/emission 420-700 nm.
Figure 15:
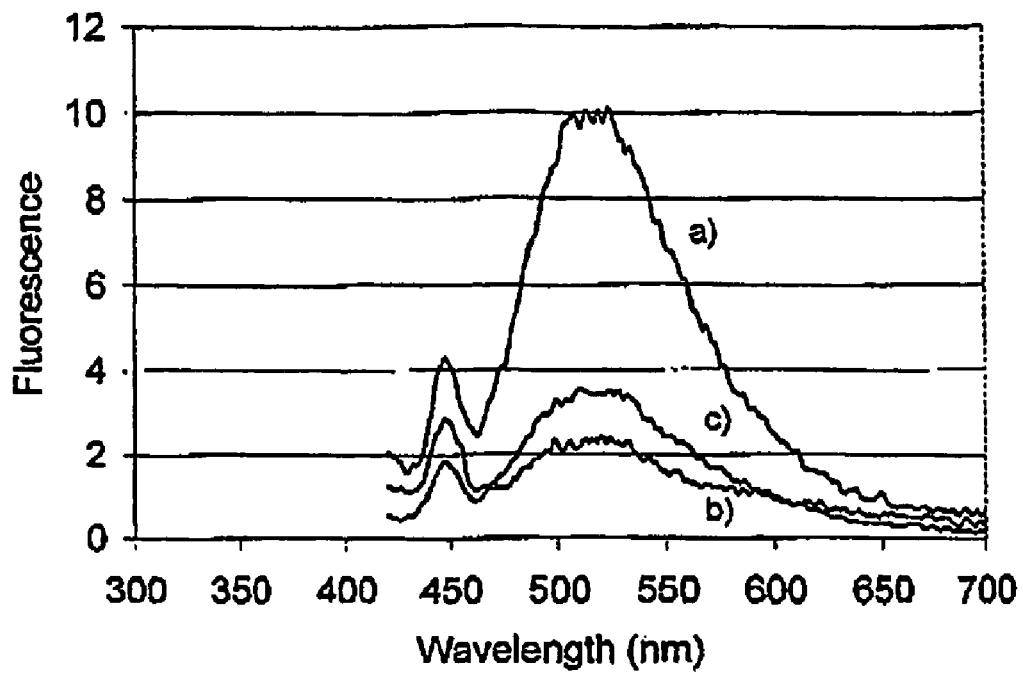
FIG. 15: Excitation 390 nm/emission 420-700 nm of a) Epicocconone with 1.625 mM DTAB and 1 mM acetic acid, b) Epicocconone with DTAB and without acid and c) Epicocconone without DTAB and without acid.
Figure 16:
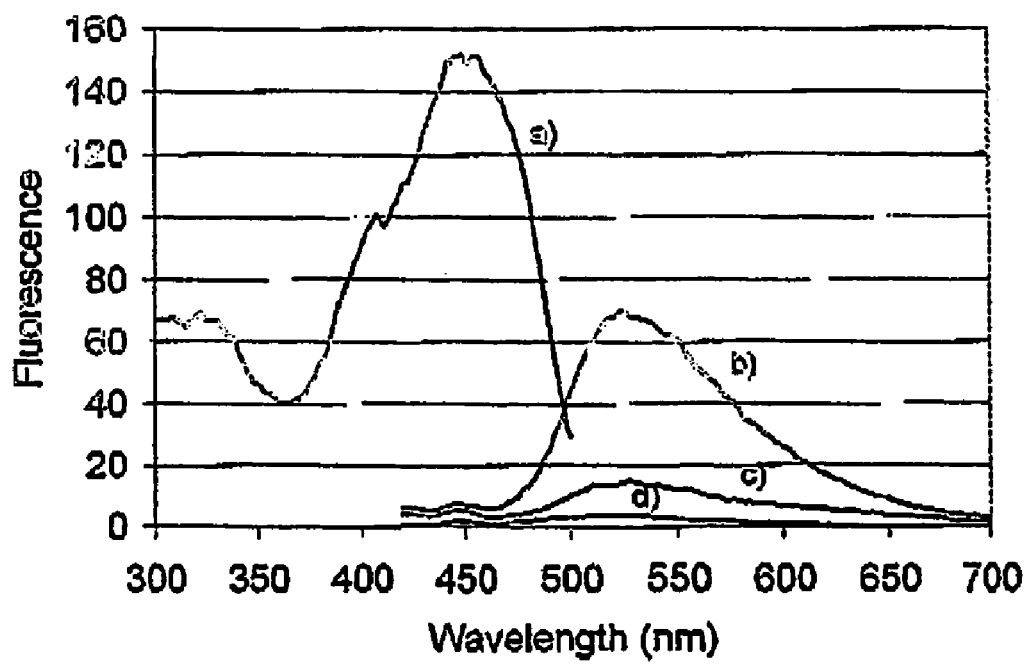
FIG. 16: a) Epicocconone with CHAPS and acetic acid: excitation 300-500 nm/emission 525 nm and b) excitation 390 nm/emission 420-700 nm compared with c) Epicocconone with CHAPS and without acid: excitation 300-500 nm/emission 528 nm and d) Epicocconone without CHAPS and without acid: excitation 390 nm/emission 420-700 nm.
Figure 17:
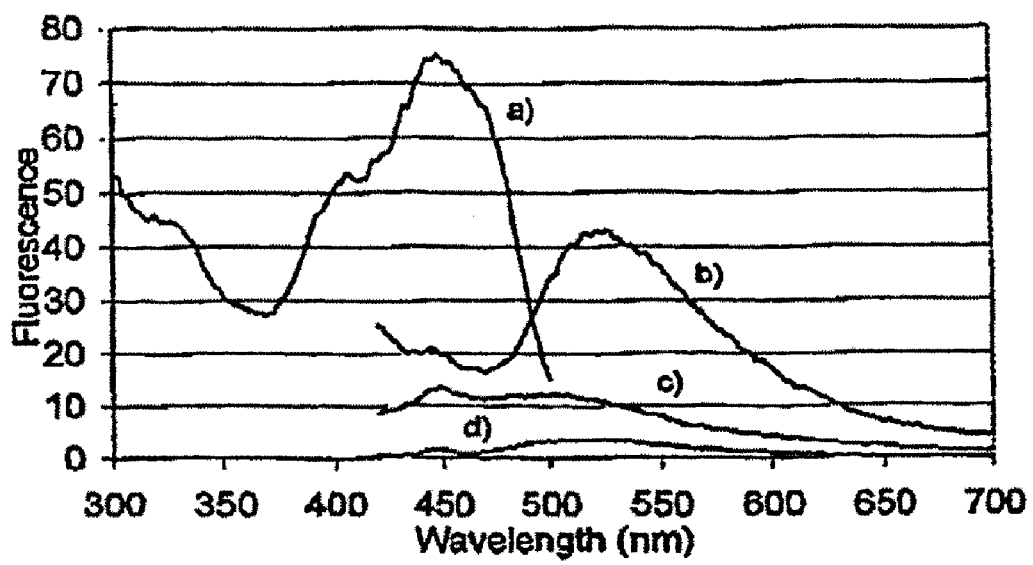
FIG. 17: a) Epicocconone with cholic acid sodium salt and acetic acid: excitation 300-500 nm/emission 525 nm and b) excitation 390 nm/emission 420-700 nm compared with c) Epicocconone with cholic acid sodium salt and without acid: excitation 390 nm/emission 420-700 nm and d) Epicocconone at the same concentration without cholic acid sodium salt and without acid: excitation 390 nm/emission 420-700 nm.

SDS (anionic detergent—final concentration of 0.03% w/v)—FIG. 13
CTAB (cationic detergent—final concentration of 1.175 mM)—FIG. 14
DTAB (cationic detergent—final concentration of 1.625 mM)—FIG. 15
CHAPS (zwitterionic detergent—final concentration of 0.0675% w/v)—FIG. 16
Cholic acid, sodium salt (anionic detergent—final concentration of 10 mM)—FIG. 17

Figure 18:
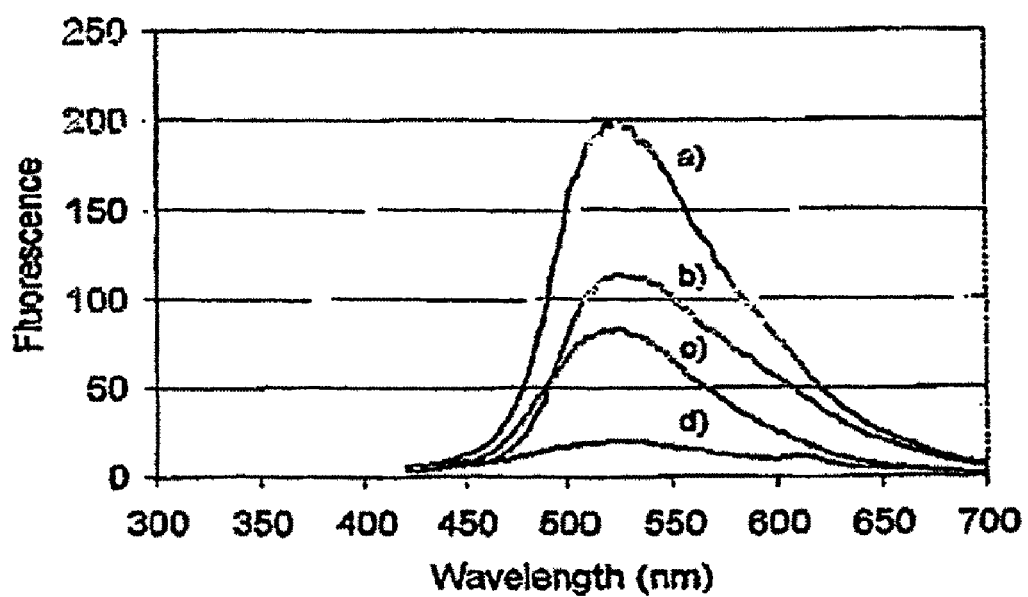
FIG. 18: Excitation 390 nm/emission 420-700 nm of a) Deep Purple™ with 0.3% SDS (w/v) and 1 mM acetic acid, b) Deep Purple™ with 0.3% SDS (w/v), c) Deep Purple™ with 1 mM AcOH and d) Deep Purple™.

The fluorescence of Deep Purple in water can also be enhanced by the combination of acetic acid and SDS (see FIG. 18).

(iv) Changes in Stokes' Shift of Epicocconone and Deep Purple™ in the Presence of Bases and Detergents Ammonia reduces the fluorescence of epicocconone. The intensity of fluorescence of this mixture can be enhanced by the addition of SDS. Generally the fluorescence is of about the same intensity as for epicocconone alone, but the emission is shifted to a longer wavelength (increased Stokes' shift). The emission at a longer wavelength can also be regarded as an enhancement as epicocconone alone generally emits weakly at the longer wavelength.

Figure 19:
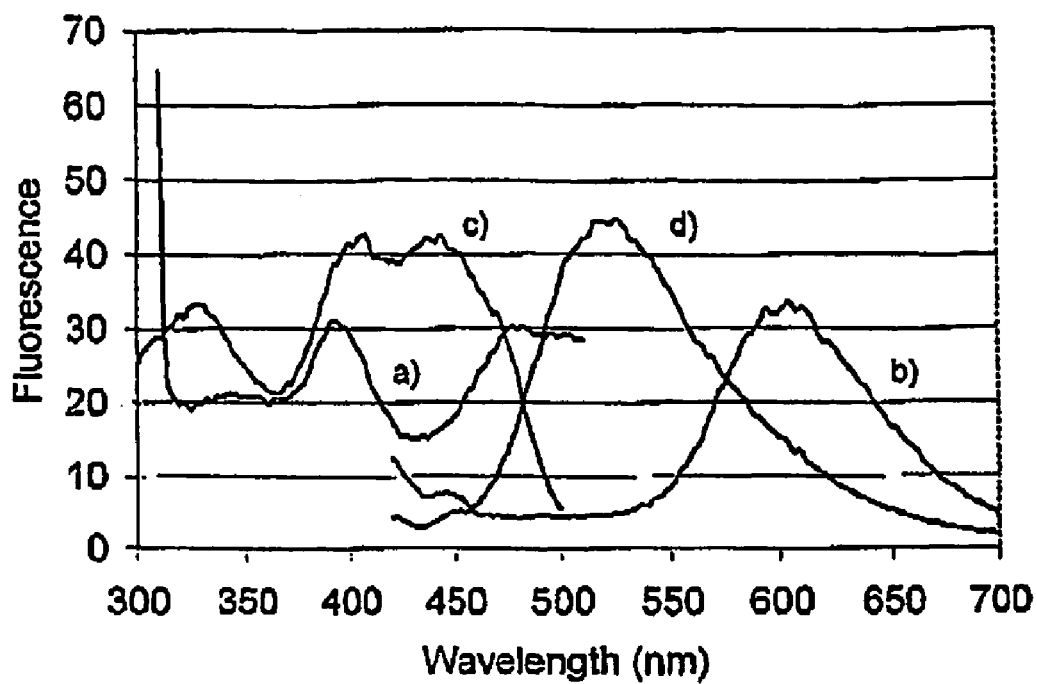
FIG. 19: a) Epicocconone with SDS and ammonia: excitation 310-500 nm/emission 605 nm and b) excitation 390 nm/emission 420-700 nm, compared with c) Epicocconone and SDS at the same concentration and without ammonia: excitation 300-500 nm/emission 520 nm and d) excitation 390 nm/emission 420-700 nm.

The fluorescence of epicocconone in water with SDS emits with a longer Stokes' shift in the presence on ammonia. When the mixture is excited at 390 nm it has an emission maximum at 605 nm. The fluorescence spectra in FIG. 19 is generated with a concentration of epicocconone of 1.4 µg/mL ($3.4 \times 10^{-6}$ M) in water and a final concentration of 0.3% SDS (w/v) and 1 mM aqueous ammonia.

Figure 20:
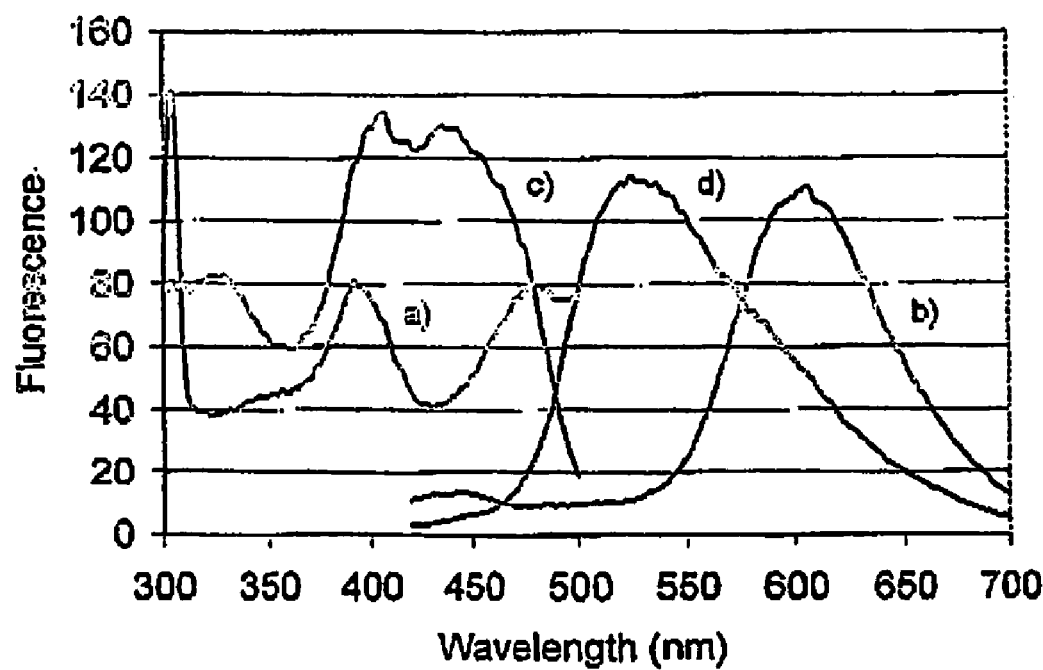
FIG. 20: a) Deep Purple™ with 0.3% SDS and 1 mM ammonia: excitation 300-500 nm/emission 605 nm and b) excitation 390 nm/emission 420-700 nm compared with c) Deep Purple™ with 0.3% SDS and without ammonia at the same concentration: excitation 300-500 nm/emission 525 nm and d) excitation 390 nm/emission 420-700 nm.
Figure 21:
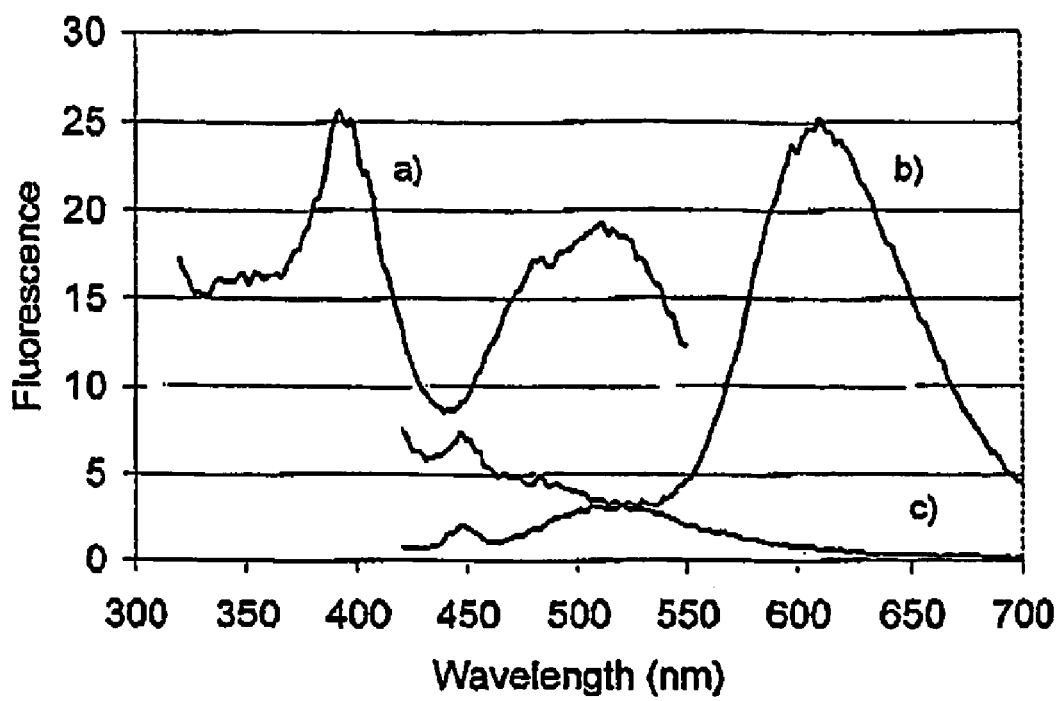
FIG. 21: a) Epicocconone with SDS and ethylamine: excitation 320-550 nm/emission 610 nm and b) excitation 390 nm/emission 420-700 nm compared with c) Epicocconone at the same concentration without SDS and without ethylamine: excitation 390 nm/emission 420-700 nm.
Figure 22:
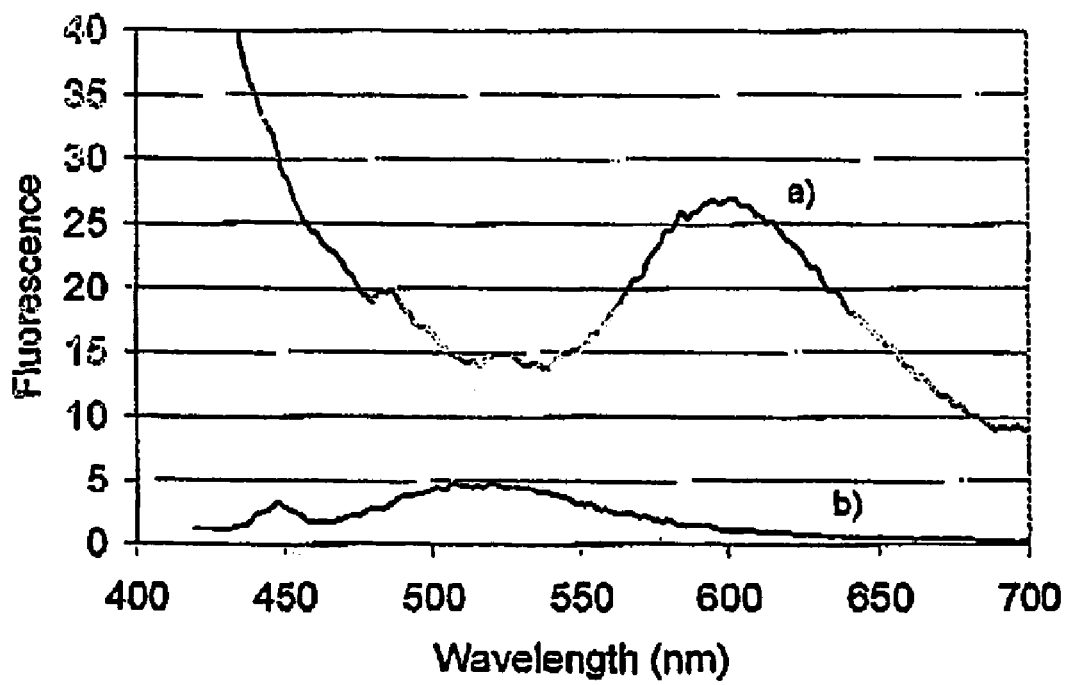
FIG. 22: a) Epicocconone with SDS and butylamine: excitation 390 nm/emission 420-700 nm compared with b) Epicocconone at the same concentration without SDS and without butylamine: excitation 390 nm/emission 420-700 mn.
Figure 23:
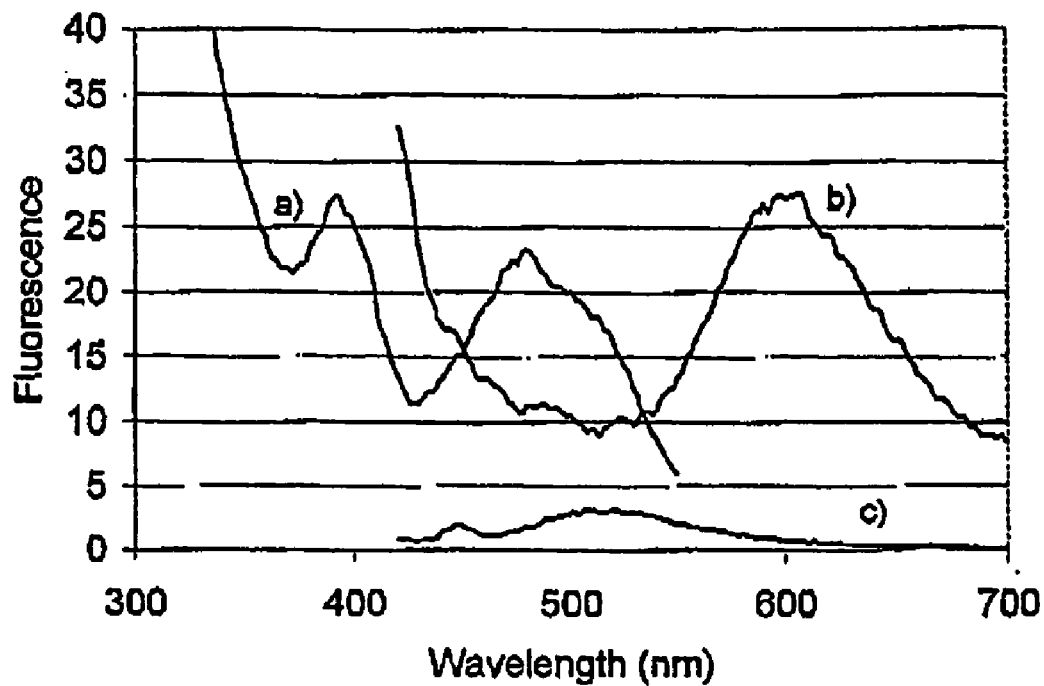
FIG. 23: a) Epicocconone with SDS and octylamine: excitation 320-550 nm/emission 600 nm and b) excitation 390 nm/emission 420-700 nm compared with c) Epicocconone at the same concentration without SDS and without octylamine: excitation 390 nm/emission 420-700 nm.

The fluorescence of Deep Purple in water with SDS can also emit with a longer Stokes' shift in the presence on ammonia. When the mixture is excited at 390 nm it has an emission maximum at 605 nm (see FIG. 20).

The Stokes' shift of epicocconone, when excited at 390 nm, can be increased by the addition of bases such as ethylamine, butylamine, octylamine, TRIS, benzylamine and aniline. The fluorescence spectra in FIGS. 21 to 26 were generated with a concentration of epicocconone of 1.05 µg/mL ($2.56 \times 10^{-6}$ M) in water and a final concentration of 0.3% SDS (w/v). The following final concentrations of the bases were used:

Ethylamine—1 mM aqueous (FIG. 21)
Butylamine—10 mM aqueous (FIG. 22)
n-Octylamine—10 mM aqueous (FIG. 23)
TRIS—100 mM aqueous (FIG. 24)
Benzylamine—10 mM aqueous (FIG. 25)
Aniline—10 mM aqueous (FIG. 26)

In this series of experiments, aniline yielded the largest Stokes' shift ($\lambda_{em}$=620 nm).

The Stokes' shift of epicocconone, when excited at 390 nm, can be increased by the addition 1,3-diaminopropane. The fluorescence spectra in FIG. 27 were recorded using a concentration of epicocconone of 1.05 µg/mL ($2.56 \times 10^{-6}$ M), 0.3% SDS, DNA (1 mg/mL) and 1 mM 1,3-diaminopropane. The emission was enhanced further when the sample was left for a day at 4° C. and re-run (see FIG. 27).

The fluorescence of epicocconone in water containing CHAPS (zwitterionic detergent) emits at a longer Stokes' shift when ammonia is added. The addition of ammonia to an epicocconone/CHAPS solution shows an increase in fluorescence at 630 nm with respect to epicocconone alone at 630 nm. The fluorescence spectra in FIG. 28 was generated with a concentration of epicocconone of 1.05 µg/mL ($2.56 \times 10^{-6}$ M) in water and a final concentration of 0.0675% CHAPS (w/v) and 1 mM aqueous ammonia.

The Stokes' shift of epicocconone/detergent mixtures, when excited at 390 nm, can be increased by the addition of bases and enhanced with acetic acid. The fluorescence spectra of FIGS. 32 to 34 were generated with a concentration of epicocconone of 1.05 µg/mL ($2.56 \times 10^{-6}$ M), final concentration of SDS of 0.3% (w/v) and final concentration of acetic acid of 1 mM. The following bases were used, at a final concentration stipulated.

Aniline—10 mM aqueous (FIG. 29)
TRIS—100 mM aqueous (FIG. 30)
Ethylamine—1 mM aqueous (FIG. 31)

In each case the addition of acetic acid further enhanced the fluorescence following an increase in Stokes' shift.

(v) Other Fluorescence Enhancements and/or Changes in the Stokes' Shift

The emission of an aqueous solution containing epicocconone, acetic acid and DTAB can be enhanced with DNA when excited at 390 nm with a concomitant Stokes' shift from 520 to 540 nm. The fluorescence spectra of FIG. 32 were recorded using a concentration of epicocconone of 1.05 µg/mL ($2.56 \times 10^{-6}$ M), 1.625 mM DTAB, 1 mM acetic acid and DNA (1 mg/mL) as a representative nucleic acid. This indicates that epicocconone, in combination with detergent and/or acid can be used in detection/analysis of DNA and other nucleic acids.

The emission of an aqueous solution containing epicocconone, CHAPS and ammonia can be enhanced with glucosamine hydrochloride when excited at 390 nm. As well as an enhancement there is an increase in the Stokes' shift. The fluorescence spectra in FIG. 33 were recorded using a concentration of epicocconone of 1.05 µg/mL ($2.56 \times 10^{-6}$ M), 0.0675% CHAPS, 1 mM ammonia and glucosamine hydrochloride (13.25 mM).

The emission of an aqueous solution containing epicocconone, DTAB can be enhanced with protein when excited at 390 nm. As well as an enhancement there is an increase in the Stokes' shift. The fluorescence spectra in FIG. 34 were recorded using a concentration of epicocconone of 1.05 μg/mL ($2.56 \times 10^{-6}$ M), 1.625 mM DTAB and BSA (1 mg/mL).

A solution of epicocconone (1.05 μg/mL; $2.56 \times 10^{-6}$ M) in acetonitrile was prepared from the stock solution of epicocconone in DMSO. epicocconone in organic solvent fluoresces more than in water ($\lambda_{em}$=520 nm) (see FIG. 35).

Summary of Emission Wavelengths for Samples Excited at 390 nm.

Epicocconone and SDS ($\lambda_{em}$=525 nm) with:

| Amine | $\lambda_{em}$ (nm) |
|---|---|
| a) Dodecylamine | 584 |
| b) Benzylamine | 600 |
| c) Butylamine | 600 |
| d) 1,6-Diaminohexane | 600/447 |
| e) Octylamine | 600 |
| f) TRIS | 600 |
| g) Ammonia | 605 |
| h) Ethylamine | 610 |
| i) Aniline | 620 |

Summary of Preliminary Results Using Other Bases

| | |
|---|---|
| Diethylamine (2° amine) | shift to red |
| Triethylamine (3° amine) | shift to red |
| Hydrazine | emissions in the green and red |
| 1,6-diaminohexane | shift to red |
| Aniline | shift to red |

The extent of the enhancement of fluorescence of epicocconone in water can be affected by the order of addition of reagents. The optimal conditions and sequence of steps will be governed by the type of analytical or quantitative technique used and can be easily determined by simple trial, to suit any such technique.

Example 2

Measurement of Protein Concentration Using Fluorescence Enhancing Combinations

Components

Part A: Deep Purple™ formulated in 80% (v/v) dimethyl sulfoxide and 20% (v/v) acetonitrile at Absorbance550 nm=0.30.

Part B: A 10× solution is prepared as shown in Table 1.

| Reagent | Concentration |
|---|---|
| SDS | 3% w/v |
| NaHCO$_3$ | 200 mM |
| Acetonitrile | 25% v/v |
| Water | 75% v/v |

A 1× working solution of the kit is prepared by mixing together 8 parts water and 1 part of each of component Part A and Part B.

Protocol

A two-fold dilution series of protein standard of bovine serum album was prepared in water over the range 10 ng/mL-100 μg/mL. Aliquots (50 μL) of protein standard are pipetted in duplicate into wells of microtitre plates. Fifty-μL aliquots of water are added as protein free controls. To each well is added an equal volume (50 μL) of 1× working solution.

Fluorescence is then allowed to develop for at least 5 min prior to measurement. Protein standards and experimental samples are prepared and incubated for equal amount of time prior to recording fluorescence.

For laser-based imaging system 532 nm laser light excitation with 610 BP 30 nm or similar emission filtering is used. For plate-based fluorescent measuring systems, such as the BMG Fluostar (BMG Labtech, Mornington, VIC, Australia), 540 nm excitation filtering together with 630-12 nm emission filtering or similar is recommended.

EXAMPLE

Sigma bovine serum albumin (Castle Hill, NSW, Australia; Cat. A3059) was suspended at a concentration of 800 μg/mL in water and two-fold diluted to final concentration of 0.76 ng/mL. Fifty-μL aliquots were plated out, in triplicate, into a Greiner (Interpath Services, West Heidelberg, VIC) 96-well plate (Cat. 655096). FIG. 36 shows an image of the microtitre plate captured by the Typhoon laser-based imager (532 nm laser, 610 BP 30 emission filter). FIGS. 37A and 37B show plots of fluorescence data plotted against BSA concentration per mL in the range of 12 ng-100 μg/mL Gel Staining Materials and Methods Invitrogen Bis-Tris 10-well 12% polyacrylamide gels were prepared and run according to the manufacturer's instructions (NuPAGE Technical Guide, Version D, Aug. 26, 2002. IM-1001). Amersham Biosciences (Castle Hill, NSW, Australia) SDS Low Molecular Weight protein markers were prepared and two-fold diluted in Invitrogen LDS sample buffer (Mt Waverly, VIC, Australia, Cat. NP0007) containing 50 mM dithiothreitol (Bio-Rad, Regents Park, NSW, Australia). Samples were heated at 70° C. for 10 minutes. Gels were separated using 1×MES (Sigma, Castle Hill, NSW, Australia; Cat M2933) buffer. Invitrogen Antioxidant (Cat. NP 0005; 500 μL) was added to the cathode chamber of the Invitrogen X-cell Sure-Lock Mini Cell and gels were run at constant 200 V until tracking dye reached the base of the gels.

The gels were fixed in 100 mL of 7.5% acetic acid (v/v) for 1 hour and gels were then washed in equal volumes of double distilled (dd) water 2×30 minutes.

Gels were then transferred to 50 mL volumes of fresh dd water and 250 μL of Deep Purple™ (Amersham Biosciences) and stained for 1 h at room temperature.

For the ammonia gel-developing step the gel stain was removed and replaced with 100 mL volumes of 8 mM (0.05% v/v) concentrated ammonia. The gels were washed for 2×10 minutes.

An acid stabilizing step then involved replacing the ammonia solution with an equal volume of 0.05% (9 mM) sulphuric acid and washing for a further 10 minutes. Gels were then ready for imaging and storage. During storage, gels were kept in the dark at room temperature.

Gels were imaged with an Typhoon imaging system (Amersham Biosciences, Castle Hill, NSW, Australia) using a 532 nm YAG laser with the photomultiplier tube set at 540 V and with 100 μm² pixel size. Either a 560 nm Long Pass or 610 Band Pass 30 nm emission filter was used for obtaining the image.

Example 3

Deep Purple™ Protein Gel Staining

1. Boosting of Intensity of Gel Stain

Protocol

Invitrogen Bis-Tris. 10% 12-well polyacrylamide gels were loaded with reduced (50 mM dithiothreitol). Amersham Biosciences Low Molecular Weight Markers prepared and heated (10 min., 70° C.) in Invitrogen 1×LDS buffer. The amounts of Soybean Trypsin Inhibitor (one of the six low molecular weight markers) loaded per 5 uL aliquot as follows:

| | Lane | | | | | | | | | |
|---|---|---|---|---|---|---|---|---|---|---|
| | 2 | 3 | 4 | 5 | 6 | 7 | 8 | 9 | 10 | 11 |
| ng | 0.125 | 0.25 | 0.5 | 1 | 2 | 16 | 32 | 64 | 128 | 256 |

Gels were run at 200 V constant and transferred to 60 mL of 7.5% (v/v) acetic acid for 30 minutes followed by three sequential 30 minute washes in 60 mL RO water. Gels were placed in 50 mL of RO water together with 250 μL Deep Purple™ and stained in dark for 1 h. Gels were independently washed 3×10 minute in 16 mM solutions listed in Table 2 and imaged with Amersham Biosciences Typhoon using 532 nm laser, a 560 LP emission filter and 520 V at the photomultiplier tube. Using ImageQuant 5.2 (Amersham Biosciences, Castle Hill, NSW, Australia) a trace was made though Lane 9 of each gel so the absolute intensity of the signal could be compared across gels.

TABLE 2

| Gel No. | 16 mM reagent |
|---|---|
| 1. | Octylamine |
| 2. | Tris base |
| 3. | Butylamine |
| 4. | Aniline |
| 5. | 1,3 diaminopropane |
| 6. | Ammonia |
| 7. | Water |

Results are shown in FIGS. 38A to G. In each case a 3×10 minute wash with the listed 16 mM reagent caused an absolute increase in fluorescent signal relative to that of a gel washed 3×10 minute in water.

2. Boosting and Stabilising Fluorescence Intensity in Gels Using Orthophosphoric Acid Protocol Invitrogen Bis-Tris 12% 10-well gels were loaded with reduced (50 mM dithiothreitol) Amersham Low Molecular Weight Markers prepared and heated (10 min., 70° C.) in Invitrogen 1×LDS buffer. Replicate gel loaded with 100 ng soybean trypsin inhibitor per lane. Gels were run in 1×MES running buffer at 200 V. Gels were then transferred to 100 mL of 7.5% (v/v) acetic acid for 1 hour followed by two sequential 30 minute washes in 100 mL RO water. Gels were then placed in 50 mL of RO water together with 250 μL Deep Purple™ and stained in dark for 1 h.

On removing the gel stain, gel segment number 1 (see FIG. 39A) was washed 3×10 minutes in 8 mM ammonia and stored in 8 mM ammonia under dark conditions for 46 h. Replicate gel segment number 2 (FIG. 39B) was washed 3×10 min. in 8 mM ammonia and transferred to 100 mM orthophosphoric acid and stored under dark conditions also for 46 h. Gels were imaged on an Amersham Bioscience Typhoon with a 532 nm laser, 560 LP filter, and 540 Volts at the photomultiplier tube.

Orthophosphoric acid increased fluorescence intensity of gels stained with epicocconone after development with ammonia (FIG. 39A) as compared to ammonia only (FIG. 39B).

3. Boosting and Stabilising Fluorescence Intensity in Gels Using Sulfuric Acid

Protocol

Storage of gels in sulfuric acid was investigated. Invitrogen Bis-Tris 10% 15-well gels were equivalently loaded with reduced (50 mM dithiothreitol) Amersham Low Molecular Weight Markers prepared and heated (10 min., 70° C.) in Invitrogen 1×LDS buffer. Replicate gels were loaded with soybean trypsin inhibitor at 100 ng in 5 μL per lane. Gels were run at 200 V constant and transferred to 100 mL of 7.5% (v/v) acetic acid for 1 hour followed by two sequential 30 minute washes in 100 mL RO water. Gels were then placed in 50 mL of RO water together with 250 μL Deep Purple™ and stained in dark for 1 h. Gels were then washed 3×10 minutes in 8 mM ammonia and imaged on the Amersham Biosciences Typhoon with a 532 nm laser, 560 LP emission filter and 540 V at the photomultiplier tube (FIG. 40A). The gels was stored at room temperature in 10 mM sulfuric acid and re-imaged as described in Example 2 after 2 h, 21 h and 93 h (FIGS. 40B-40D). Intensity traces were plotted of the same lane of the gel at different time-points (FIGS. 40E-40H). FIGS. 40 E-H show signal intensity trace of Lane 3 of the gel above prior to placing in 10 mM sulfuric acid (E, Time 0) and at 2 h (F), 21 h (G) and 93 h (H) after addition of 10 mM sulfuric acid. Note increase in stain intensity at 2 h.

Result 10 mM sulfuric acid after increased in the intensity of fluorescence over and above that produced by ammonia washes post-staining. Storage of the gel in sufuric acid maintained the signal at levels higher than if gel were in stored in 8 mM ammonia or water.

4. Boosting and Stabilising Fluorescence Intensity in Gels Using Acetic Acid

Storage of gels in acetic acid was investigated. Invitrogen Bis-Tris 12% 10-well gels were equivalently loaded with reduced (50 mM dithiothreitol) Amersham Biosciences Low Molecular Weight Markers where soybean trypsin inhibitor was at a concentration of 400 ng/5 μL. The protein samples were two-fold diluted to final concentration of 0.76 ng/5 μL and heated (10 min., 70° C.) in Invitrogen 1×LDS buffer and loaded into gels. Gels were run at 200 V constant and transferred to 100 mL of 7.5% (v/v) acetic acid for 1 hour followed by two sequential 30 minute washes in 100 mL RO water. Gels were then placed in 50 mL of RO water together with 250 μL Deep Purple™ and stained in dark for 1 h. On removing the gel stain, the gel was washed 2×10 minutes in 8 mM ammonia and imaged on an Amersham Biosciences Typhoon with 532 nm laser, 560 LP emission filter and 560 V at the photomultiplier tube (FIG. 41A). The gel was placed in 10 mM acetic acid and re-imaged after 46 h and 167 h (FIGS. 41B-41C).

Result 10 mM acetic acid after washes in 8 mM ammonia resulted in an increase in the stain intensity over and above that produced by ammonia washes post-staining. Storage of the gel in acetic acid maintained the signal at levels higher than if gel were in stored in 8 mM ammonia or water.

Example 4

Epicocconone-Staining of DNA Fragments in an Agarose Gel: The Effect of Detergent on Epicocconone-Staining Materials
Epicocconone (0.042 mg/ml DMSO)
DNA fragments:: SPP-1 Phage/Eco RI (cat DWM-S1, Geneworks), DNA Molecular
Weight Marker XVII (cat # 1855646, Roche).
DTAB (1.625 mM)
TDTAB (0.001, 0.01, 0.1 and 1 mM)
CTAB (0.001, 0.01, 0.1 and 1 mM)
CPC (0.001, 0.01, 0.1 and 1 mM)
SDS (1.625 mM)
Acetic acid (1 mM)
Reverse Osmosis (RO) water
Agarose gel (1.5%) (DNA grade agarose, Progen)
TAE electrophoresis buffer (Tris-acetate/EDTA, pH 8.3)
DNA sample loading buffer (cat number 200-0424, Progen)

DTAB, TDTAB, CTAB and CPC were used in this nucleic acid experiment as suitable examples of cationic detergents which, because of their cationic nature, are likely to react appropriately with DNA[11,12]. The relevant publications are incorporated herein by reference. SDS was used as an example of an anionic detergent which, although useful in protein methodology, is unlikely to react appropriately with nucleic acid.

Staining Method
1. DNA molecular marker samples were prepared in Progen sample loading buffer. The concentration was adjusted to 1000 ng/sample. The samples were loaded into an agarose gel (1.0% or 1.5%) and run at 100 V for 1.5 hours.
2. After running the gel, the gel was rinsed off in 1-L of RO water.
3. Lanes of the DNA gel were cut into strips.
4. Each gel strip containing DNA fragments was then placed into a 15-mL Falcon tube containing 10-mL of varying concentrations of different cationic detergents specified in the material section. The detergent incubation was done at room temperature for 30 min.
5. After 30-min-incubation, the initial incubating solutions were decanted from each tube. Ten milliliter of epicocconone staining solution made in RO water (0.0042 mg/mL) was then replaced into the tubes. The gel strip tubes were stained at room temperature (dark) for 1 hour.
6. After 1-hour-epicocconone staining, the staining solution was decanted, replaced with 10-mL of acetic acid (1 mM), and incubated at room temperature for 30 min (three times of 10-min-incubation).
7. After acetic acid-treatment, the gel strips were scanned by Typhoon scanner (Model 9200, Amersham Biosciences). The scanning conditions were: 550 V, normal sensitivity, and 610 BP 30/Green (532 nm).

Results

FIG. 42 shows Typhoon-scanned images of the DNA gel (SPP-1 DNA/Eco RI) strips (1: No detergent treatment, epicocconone staining only; 2: SDS (1.625 mM)-incubation and epicocconone staining; 3: DTAB (1.625 mM)-incubation and epicocconone staining; 4: SDS and DTAB-incubation, and epicocconone staining).

1. The molecular DNA bands of gel strip 1 were not stained with epicocconone only.
2. The molecular DNA bands of gel strip 2 were not stained with epicocconone when the DNA had been initially incubated with SDS.
3. The molecular DNA bands of gel strip 3 were stained with epicocconone when the DNA had been initially incubated with DTAB.
4. The molecular DNA bands of gel strip 4 were stained with epicocconone when the DNA had been initially incubated with SDS and DTAB.

FIG. 47 shows Typhoon-scanned images of the DNA gel (A and C, DNA MWM XVII; B, SPP-1 DNA/Eco RI) strips. FIG. 47-A, the DNA gel strips that were pre-incubated in TDTAB (1, 0.001 mM; 2, 0.01 mM, 0.1 mM and 1 mM) before epicocconone staining; FIG. 47-B, the DNA gel strips that were pre-incubated in CTAB (1, 0.001 mM; 2, 0.01 mM, 0.1 mM and 1 mM) before epicocconone staining; FIG. 47-C, the DNA gel strips that were pre-incubated in CPC (1, 0.001 mM; 2, 0.01 mM, 0.1 mM and 1 mM) before epicocconone staining.

1. TDTAB pre-incubation stained DNA fragments with epicocconone, when the detergent concentration was ranged from 0.1 to 1 mM.
2. CTAB pre-incubation stained DNA fragments with epicocconone, when the detergent concentration was ranged from 0.01 to 0.1 mM.
3. CPC pre-incubation stained DNA fragments with epicocconone, when the detergent concentration was ranged from 0.01 to 0.1 mM.

Conclusion
1. The anionic detergent used (SDS) did not aid staining of DNA with epicocconone whereas different cationic detergents (DTAB, TDTAB, CTAB, and CPC) were effective in revealing DNA fragments stained with epicocconone.
2. The present experiment shows that epicocconone can be used as a DNA and other nucleic acid stain when they are treated with a wide range of different cationic detergents such as DTAB, TDTAB, CTAB, and CPC.

Other suitable cationic detergents may be used and will be known to those skilled in the art. Some of these detergents are disclosed in, for example, Bhairi SM, incorporated herein by reference[17], but other sources of suitable detergents and surfactants will be know to those skilled in the art.

Although DNA was used as a convenient and stable example of a nucleic acid because of ease of handling, the above principles apply equally well to RNA and other nucleic acids and their derivatives, including single and double stranded nucleic acids. Further, these concepts and principles can be applied to a number of known nucleic acid analytical and quantitative techniques, such as for example those described in Old RW and Primrose SB[4], Innis MA et al[15] and Sambrook J et al[16]

Example 5

Measurement of DNA Concentration

Components

Deep Purple™ formulated in 80% (v/v) dimethyl sulfoxide and 20% (v/v) acetonitrile at Absorbance550 nm=0.30.

Protocol

Salmon double stranded DNA (Sigma, D1626) was prepared at a concentration of 500 μg/mL in water and two-fold diluted in water to a final concentration of 488 ng/mL. Aliquots (25 μL) of DNA were pipetted in duplicate into the wells of a 96-well microtitre plate (Greiner, Cat. 655096). 25 μL aliquots of water were also included as DNA-free controls.

To duplicate rows of the plate were then added 25 μL of the cationic surfactant dodecyl trimethyl ammonium bromide (Sigma, D5047) at concentration of 3 mM in water. To individual rows was then added, depending on the particular experiment, 25 μL aliquots of, 10 mM acetic acid, 10 mM ammonia solution, or 40 mM $NaHCO_3$. To wells were then added 25 μL aliquot of Part A diluted 1:10 in water. Plates were incubated in dark for approximately 30 minutes and visualised on a UVA and UVB transilluminators and imaged on an Amersham Bioscience Typhoon with a 532 nm excitation laser and either a 560 LP or 526 SP emission filter to measure red and green emission light respectively.

By the above procedure it was possible to quantify DNA in solution. For results see FIGS. 43, 44A-44B, 45 and 46A-46B. FIG. 43 shows a Typhoon image of red emission light. 532 nm laser, 560 LP filter. After addition of stain, 10 mM ammonia solution added to wells after addition of Deep Purple formulated as described in Protocol. FIGS. 44A shows signal from FIG. 43 plotted as raw data. FIG. 44B is a plot of the $log_{10}$ transformed data. FIG. 45 is a Typhoon image of green emission light. 532 nm laser, 526 SP filter. After addition of stain, 10 mM acetic acid solution added to wells after addition of Deep Purple formulated as described in Protocol. On UVA and UVB transilluminators the intensity of the wells treated with acetic acid was intensely bright green and substantially brighter than the red fluorescence from wells treated with 10 mM ammonia or 40 mM $NaHCO_3$. Due to its hardware configuration the Typhoon instrument was poor at exciting and capturing this information. FIG. 46A is a signal from FIG. 45 plotted as raw data. FIG. 46B is a plot of the same data transformed $log_{10}$.

The results clearly indicate the utility of the dye and the use of detergents and/or bases and/or acids in improving detection and quantitation of nucleic acids.

The present invention has been described with reference to specific examples. The skilled person will appreciate that the inventions may be embodied in many other forms, in keeping with the spirit of the inventive concept described herein.

REFERENCES

1 Hames, B. D. (1990) One-dimensional polyacrylamide gel electrophoresis, in "Gel electrophoresis of proteins: a practical approach" Second Ed., (Eds, B. D. Hames and D. Rickwood). pp. 1-139. IRL Press, Oxford 2 Bartoszek A, Sielenko A and Wesiora M. (2003). Versatile method employing basic techniques of genetic engineering to study the ability of low-molecular-weight compounds to bind covalently with DNA in cell-free systems. *Anal Biochem.* 313(1):53-9

3. Jaroszeski M J, Gilbert R and Heller R (1994). Detection and quantitation of cell-cell electrofusion products by flow cytometry. *Anal Biochem* 216: 271-275

4. Kamp F, Guo W, Souto R, Pilch P F, Corkey B E and Hamilton J A (2003). Rapid flip-flop of oleic acid across the plasma membrane of adipocytes. *J Biol Chem* 278: 7988-95

5. Paulmurugan R, Massoud T F, Huang J and Gambhir S S (2004). Molecular imaging of drug-modulated protein-protein interactions in living subjects. *Cancer Res.* 64:2113-2119.

6. Kersten B, Feilner T, Kramer A, Wehrmeyer S, Possling A, Witt I, Zanor M I, Stracke R, Lueking A, Kreutzberger J, Lehrach H, Cahill D J. (2003). Generation of *Arabidopsis* protein chips for antibody and serum screening. *Plant Mol Biol.* 52:999-1010.

7 Breadmore M C, Wolfe K A, Arcibal I G, Leung W K, Dickson D, Giordano B C, Power M E, Ferrance J P, Feldman S H, Norris P M and Landers J P (2003). Microchip-based purification of DNA from biological samples. *Anal Chem.* 75:1880-1886.

8 Ferrari B C, Attfield P V, Veal D A and Bell P J. (2003). Application of the novel fluorescent dye Beljian red to the differentiation of Giardia cysts. *J Microbiol Methods.* 52:133-5.

9 Graczyk T K, Grimes B H, Knight R, Da Silva A J, Pieniazek N J, Veal D A. (2003). Detection of *Cryptosporidium parvum* and *Giardia lamblia* carried by synanthropic flies by combined fluorescent in situ hybridization and a monoclonal antibody. *Am J Trop Med Hyg.* 68:228-232

10 Shapiro, H. M. 2003 Practical Flow Cytometry, Forth Edition, John Wiley, New Jersey.

11 Bathaie S Z, Moosavi-Movahedi A A, Saboury A A. (1999). Energetic and binding properties of DNA upon interaction with dodecyl trimethylammonium bromide. *Nucleic Acids Res.* 1999 Feb. 15; 27(4):1001-5.

12 Harrington L A, and Andrews, B J. (1996) Binding to the yeast Swi4,6-dependent cell cycle box, CACGAAA, is cell cycle regulated in vivo *Nucleic Acids Res.* 24:558-565.

13 Bell P J L and Karuso P, (2003), Epicocconone, A Novel Fluorescent Compound from the Fungus *Epicoccum nigrum. J Am Chem Soc,* 125: 9304-9305.

14 Old R W and Primrose S B, Principles of Gene manipulation: An Introduction to genetic engineering, Blackwell Scientific Publications, 4$^{th}$ Edition, 1989.

15 Innis M A, Gelfand D H, Sninsky J J and White T J, PCR Protocols: A guide to methods and applications. Academic Press Inc, 1990

16 Sambrook J, Fritsch E F and Maniatis T. Molecular cloning, a laboratory manual. Cold Spring Harbor Laboratory Press, NY, 1989.

17 Bhairi S M. Detergents: A guide to the properties and uses of detergents in biological systems, Calbiochem-Novabiochem Corp., 2001

What is claimed is:

1. A method of enhancing the fluorescence of a fluorescent dye, said method comprising combining or contacting the dye with a base and/or a detergent, wherein the dye is of formula (Ia), including isomers thereof:

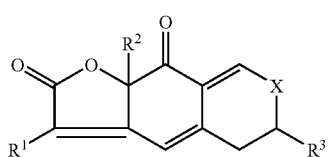

(Ia)

wherein X is O, $NR^4$ or C, $R^1$ is a straight or branched chain $C_{1-20}$ conjugated alkenyl group optionally substituted 1-6 groups independently selected from hydroxy or oxo groups, $R^2$ is a straight or branched chain $C_{1-20}$ alkyl group, $R^3$ is a straight or branched chain $C_{1-20}$ alkyl group, optionally substituted with a hydroxyl group, $R^4$ is N, O, straight or branched chain $C_{1-20}$ alkyl and/or aryl group, optionally substituted with a hydroxyl, halide, amine, carboxyl, carboxyl related or heteroaryl group or groups.

2. The method of claim 1, wherein $R^2$ is a straight or branched chain $C_{1-20}$ alkyl group.

3. The method of claim 1, wherein $R^3$ is a straight or branched chain $C_{1-20}$ alkyl group, optionally substituted with a hydroxyl group.

4. The method of claim 1, wherein the dye is of formula (Ib), including isomers thereof:

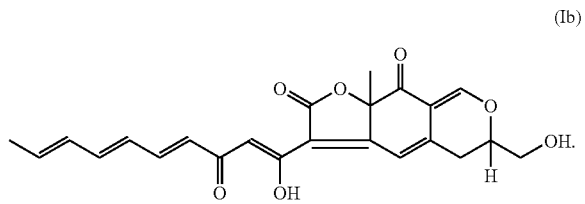

(Ib)

5. A method of enhancing the fluorescence of a fluorescent dye, said method comprising combining or contacting they dye with a base and/or a detergent, wherein the fluorescent dye is an azaphilone fluorescent dye.

6. The method of claim 1, wherein the isomer is a tautomer.

7. The method of claim 1 wherein the fluorescent dye is epicocconone or an epicocconone-containing dye mixture or extract.

8. A method of enhancing the fluorescence of a fluorescent dye, said method comprising combining or contacting they dye with a base and/or a detergent, wherein the base is a nitrogen-containing base.

9. The method of claim 8, wherein the base is selected from the group consisting of ammonia, amines, metal hydroxides, metal carbonates, metal hydrogen carbonates or combinations thereof.

10. The method of claim 8, wherein in the base is selected from ammonia, $C_{1-20}$ alkylamines, $C_{1-20}$ alkyldiamines, $C_{1-20}$ amines and diamines, such as methylamine, ethylamine, propylamine, butylamine, ethylamine, propylamine, butylamine, pentylamine, hexylamine, heptylamine, octylamine, nonylamine, decylamine, undecylamine, dodecylamine and their isomers and allyl amine, aniline, benzylamine, 2-phenylethylamine, 4-phenylbutylamine, hydrazine and 1,2-diaminoethane, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,12-diaminododecane and their isomers and dimethylamine, diethylamine, dipropylamine, dibutylamine, dipentylamine, dihexylamine, dioctylamine, didecylamine, N-methylaniline, N-ethylaniline, N-propyl aniline, N-butylaniline and their isomers and trimethylamine, triethyl amine, tripropylamine, tributylamine, tripentylamine, trihexylamine, trioctylamine, tridecylamine, tridodecylamine and their isomers and tetramethylammonium acetate, tetramethylammonium bromide, tetramethyl ammonium carbonate, tetramethylammonium chloride, tetramethylammonium fluoride, tetramethylammonium formate, tetramethylammonium hydrogensulphate, tetramethylammonium iodide, tetramethylammonium iodide, tetramethyl ammonium nitrate, tetramethylammonium sulfate, tetraethyl ammonium acetate, tetraethylammonium bromide, tetraethylammonium chloride, tetraethylammonium cyanide, tetraethylammonium fluoride, tetraethylammonium hydroxide, tetraethyl ammonium iodide, tetraethylammonium nitrate, tetrapropylammonium bromide, tetrapropyl ammonium hydroxide, tetrabutyl ammonium hydroxide, tetrabutylammonium iodide, pyrrolidine, piperidine, pyridine, imidazole, indole, purine, quinoline, pyrimidine, pyrazole, tris (hydroxymethyl)aminomethane ("Tris") or aminododecylamine or combinations thereof.

11. The method of claim 8, wherein the base increases the fluorescent intensity, the signal to background ratio and/or the sensitivity detection limit of the fluorescent dye.

12. The method of claim 8 which is part of a method of staining or labelling a protein, a peptide, a nucleic acid or a nucleotide said method comprising forming a fluorescent complex between a protein, a peptide, a nucleic acid or a nucleotide and the fluorescent dye, wherein the fluorescent complex is formed in the presence of a base or the fluorescent complex is treated with a base after its formation.

13. The method of claim 12, wherein the protein, peptide, nucleic acid or nucleotide is included in a tissue or a cell.

14. The method of claim 1, which is part of a method of mobilising and detecting a protein, a peptide, a nucleic acid or a nucleotide on a matrix.

15. The method of claim 14, which is electrophoresis on a polyacrylamide gel or an agarose gel matrix.

16. The method of claim 15, wherein the protein, peptide, nucleic acid or nucleotide is pretreated with a detergent to form an organic molecule/detergent complex.

17. The method of claim 16, wherein the detergent is selected from anionic, cationic or switterionic detergent.

18. The method of claim 17 wherein the detergent is selected from the group consisting of sodium dodecyl sulfate (SDS), lithium dodecyl sulfate (LDS), Triton, Tween, CHAPS, CTAB, DTAB, TDTAB, CPC, cholic acid and Octyl-D-glucoside.

19. The method of claim 14, wherein the gel matrix, the detergent or the protein, peptide, nucleic acid or nucleotide is treated with the base prior to electrophoresis.

20. The method of claim 19, wherein the base is a fatty amine.

21. The method of claim 14, wherein the gel matrix or the protein, peptide, nucleic acid or nucleotide is treated with the base after electrophoresis.

22. The method of claim 12, further comprising the step of treating the fluorescent complex with an acid.

23. The method of claim 22, wherein the acid treatment stabilises the fluorescent complex, further increases the fluorescent intensity or further increases the signal to background ratio of the fluorescent complex.

24. The method of claim 22, wherein the acid is a selected from a mineral acid, an organic acid, or combinations thereof.

25. The method of claim 24, wherein the mineral acid is selected from sulphuric acid, hydrochloric acid, nitric acid, phosphoric acid, orthophosphoric acid.

26. The method of claim 24, wherein the organic acid is selected from an alkanoic acid, a halogenoalkanoic acid, ascorbic acid or triflic acid.

27. The method of claim 26, wherein the alkanoic acid is selected from acetic acid or propionic acid, and the halogenoalkanoic acid is selected from trichloroacetic acid, chloroacetic acid or trifluoroacetic acid.

28. A fluorescent compound obtainable by combining a fluorescent dye of formula (Ia), including isomers thereof:

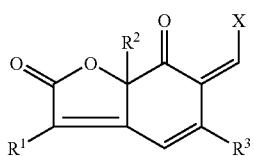

IIa wherein X is O, $NR^4$ or C, $R^1$ is a straight or branched chain $C_{1-20}$ conjugated alkenyl group optionally substituted 1-6 groups independently selected from hydroxy or oxo groups, $R^2$ is a straight or branched chain $C_{1-20}$ alkyl group, $R^3$ is a straight or branched chain $C_{1-20}$ alkyl group, optionally substituted with a hydroxyl group, $R^4$ is N, O, straight or branched chain $C_{1-20}$ alkyl and/or aryl group, optionally substituted with a hydroxyl, halide, amine, carboxyl, carboxyl related or heteroaryl group or groups with a nitrogen-containing base.

29. A fluorescent complex comprising the combination of claim 28 and, further comprising a protein, a peptide, a nucleic acid or a nucleotide and the fluorescent dye, wherein the fluorescent complex is formed in the presence of a base or the fluorescent complex is treated with a base after its formation.

30. The combination of claim 29, wherein the protein, peptide, nucleic acid or nucleotide is in the form of a complex with a detergent.

31. A method according to claim 1 wherein the fluorescent dye (Ia) combines with a base to afford a compound of the formula (IIa), including isomers thereof:

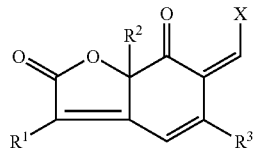

IIa wherein $R^1$, $R^2$, $R^3$ are the same as set out for (1a), X is C, $NR^4R^5$, $OR^4$, $R^4$, $R^5$ are either H, N, O, straight or branch chain $C_{1-20}$ alkyl, alkenyl, alkynyl and/or aryl group, optionally substituted with a hydroxyl, halide, amine, carboxyl, carboxyl related or heteroaryl group or groups.

32. A method according to claim 4 wherein the fluorescent dye (Ib) combines with a base to afford another fluorescent dye, which is of the formula (IIb), including isomers thereof:

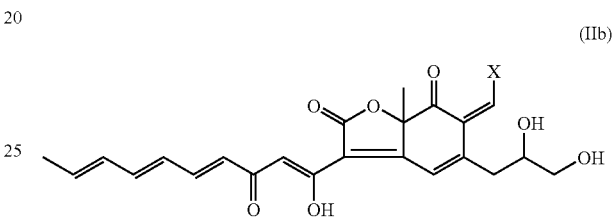

(IIb)

wherein X is C, NR4R5 or OR4.

33. A method according to claim 4 wherein when the fluorescent dye (Ib) combines with n-butylamine the resulting dye has the formula (IIc), including isomers thereof:

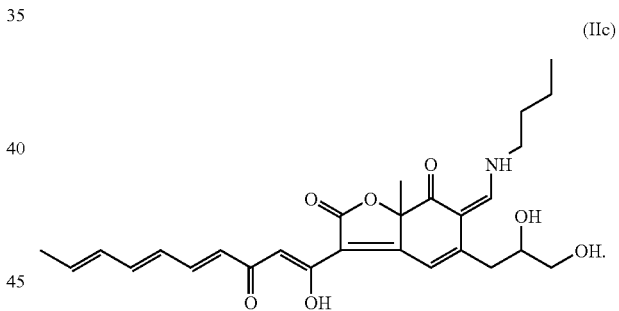

(IIc)

* * * * *